US007846476B2

(12) United States Patent
Oshlack et al.

(10) Patent No.: US 7,846,476 B2
(45) Date of Patent: Dec. 7, 2010

(54) ONCE-A-DAY OXYCODONE FORMULATIONS

(75) Inventors: Benjamin Oshlack, New York, NY (US); Curtis Wright, Norwalk, CT (US); Derek Prater, Cambridge (GB)

(73) Assignee: Purdue Pharma L.P., Stamford, CT (US)

( * ) Notice: Subject to any disclaimer, the term of this patent is extended or adjusted under 35 U.S.C. 154(b) by 1600 days.

(21) Appl. No.: 10/476,409

(22) PCT Filed: May 2, 2002

(86) PCT No.: PCT/US02/14024

§ 371 (c)(1),
(2), (4) Date: Apr. 15, 2004

(87) PCT Pub. No.: WO02/087512

PCT Pub. Date: Nov. 7, 2002

(65) Prior Publication Data

US 2004/0170680 A1    Sep. 2, 2004

Related U.S. Application Data

(60) Provisional application No. 60/288,211, filed on May 2, 2001.

(51) Int. Cl.
*A61K 9/24* (2006.01)
*A61K 9/48* (2006.01)
*A61K 9/20* (2006.01)
*A61K 9/22* (2006.01)
*A61K 9/26* (2006.01)
*A61K 9/52* (2006.01)

(52) U.S. Cl. .................. 424/457; 424/451; 424/464; 424/468; 424/469; 424/470; 424/472; 424/473; 424/474

(58) Field of Classification Search .................. None
See application file for complete search history.

(56) References Cited

U.S. PATENT DOCUMENTS

| | | | | |
|---|---|---|---|---|
| 2,738,303 | A | 3/1956 | Blythe | 167/82 |
| 2,921,883 | A | 1/1960 | Reese et al. | 167/82 |
| 3,082,154 | A | 3/1963 | Allan | 167/82 |
| 3,492,397 | A | 1/1970 | Peters et al. | 424/20 |
| 3,773,920 | A | 11/1973 | Nakamoto et al. | 424/19 |
| 3,922,339 | A | 11/1975 | Shear | 424/22 |
| 3,965,256 | A | 6/1976 | Leslie | 424/22 |
| 4,327,725 | A | 5/1982 | Cortese et al. | |
| 4,443,428 | A | 4/1984 | Oshlack et al. | 424/22 |
| 4,455,143 | A | 6/1984 | Theeuwes et al. | 604/890 |
| 4,708,874 | A | 11/1987 | De Haan et al. | 424/470 |
| 4,722,815 | A | 2/1988 | Shibanai | 264/117 |
| 4,828,836 | A | 5/1989 | Elger et al. | 424/419 |
| 4,834,984 | A | 5/1989 | Goldie et al. | 424/488 |
| 4,834,985 | A | 5/1989 | Elger et al. | 424/488 |
| 4,844,909 | A | 7/1989 | Goldie et al. | 424/480 |
| 4,861,598 | A | 8/1989 | Oshlack | 424/468 |
| 4,970,075 | A | 11/1990 | Oshlack | 424/451 |
| 4,990,341 | A | 2/1991 | Goldie et al. | 424/484 |
| 5,026,560 | A | 6/1991 | Makino et al. | 424/494 |
| 5,030,400 | A | 7/1991 | Danielsen et al. | 264/101 |
| 5,068,110 | A | 11/1991 | Fawzi et al. | 424/461 |
| 5,071,646 | A | 12/1991 | Malkowska et al. | 424/497 |
| 5,098,718 | A | 3/1992 | Ardaillon et al. | 426/2 |
| 5,122,384 | A | 6/1992 | Paradissis et al. | 424/451 |
| 5,126,145 | A | 6/1992 | Evenstad et al. | 424/465 |
| 5,132,142 | A | 7/1992 | Jones et al. | 427/196 |
| 5,133,974 | A | 7/1992 | Paradissis et al. | 424/480 |
| 5,167,964 | A | 12/1992 | Muhammad et al. | 424/482 |
| 5,169,645 | A | 12/1992 | Shukla et al. | 424/499 |
| 5,178,868 | A | 1/1993 | Malmqvist-Granlund et al. | 424/490 |
| 5,196,203 | A | 3/1993 | Boehm | 424/469 |
| 5,202,128 | A | 4/1993 | Morella et al. | 424/469 |
| 5,206,030 | A | 4/1993 | Wheatley et al. | 424/490 |
| 5,215,758 | A | 6/1993 | Krishnamurthy | 424/488 |
| 5,219,575 | A | 6/1993 | Van Bommel et al. | 424/490 |
| 5,248,516 | A | 9/1993 | Wheatley et al. | 427/3 |
| 5,258,436 | A | 11/1993 | Wheatley et al. | 524/388 |
| 5,266,331 | A | 11/1993 | Oshlack et al. | 424/468 |
| 5,273,760 | A | 12/1993 | Oshlack et al. | 424/480 |
| 5,283,065 | A | 2/1994 | Doyon et al. | 424/467 |
| 5,286,493 | A | 2/1994 | Oshlack et al. | 424/468 |
| 5,292,461 | A | 3/1994 | Juch et al. | 264/37 |

(Continued)

FOREIGN PATENT DOCUMENTS

| | | |
|---|---|---|
| AU | 9047732 | 7/1990 |
| AU | 9341654 | 2/1995 |
| CA | 635283 | 6/1982 |
| CA | 2082573 | 11/1992 |
| CA | 2131350 | 1/1994 |
| EP | 0097523 A2 | 6/1983 |
| EP | 0097523 A3 | 6/1983 |
| EP | 0097523 B1 | 6/1983 |
| EP | 0 097 523 | 1/1984 |
| EP | 0108218 A2 | 5/1984 |
| EP | 0147780 A2 | 7/1985 |

(Continued)

OTHER PUBLICATIONS

"Hydrocodone" entry in Wikipedia (http://en.wikipedia.org/wiki/Hydrocodone).*

(Continued)

*Primary Examiner*—Shanon A Foley
(74) *Attorney, Agent, or Firm*—Davidson, Davidson & Kappel LLC

(57) ABSTRACT

The invention is directed to sustained release formulations containing oxycodone or a pharmaceutically acceptable salt thereof which provide a mean $C_{24}/C_{max}$ oxycodone ratio of 0.6 to 1.0 or 0.7 to 1 after oral administration at steady state to patients and methods thereof.

17 Claims, No Drawings

U.S. PATENT DOCUMENTS

| | | | |
|---|---|---|---|
| 5,321,012 A | 6/1994 | Mayer et al. | 514/25 |
| 5,330,766 A | 7/1994 | Morella et al. | 424/490 |
| 5,356,467 A | 10/1994 | Oshlack et al. | 106/153 |
| 5,378,474 A | 1/1995 | Morella et al. | 424/469 |
| 5,384,130 A | 1/1995 | Kamada | 424/461 |
| 5,411,745 A | 5/1995 | Oshlack et al. | 424/456 |
| 5,456,923 A | 10/1995 | Nakamichi et al. | 424/489 |
| 5,460,826 A | 10/1995 | Merrill et al. | 424/470 |
| 5,472,712 A | 12/1995 | Oshlack et al. | 424/480 |
| 5,478,577 A * | 12/1995 | Sackler et al. | 424/489 |
| 5,500,227 A | 3/1996 | Oshlack et al. | 424/476 |
| 5,502,058 A | 3/1996 | Mayer et al. | 514/289 |
| 5,508,042 A | 4/1996 | Oshlack et al. | 424/468 |
| 5,508,403 A | 4/1996 | Akiyama et al. | 544/337 |
| 5,520,931 A | 5/1996 | Persson et al. | 424/473 |
| 5,549,912 A | 8/1996 | Oshlack et al. | 424/468 |
| 5,580,578 A | 12/1996 | Oshlack et al. | 424/468 |
| 5,593,695 A | 1/1997 | Merrill et al. | 424/480 |
| 5,601,842 A | 2/1997 | Bartholomaeus | 424/464 |
| 5,614,218 A | 3/1997 | Olsson et al. | 424/490 |
| 5,629,011 A | 5/1997 | Illum | 424/434 |
| 5,637,320 A | 6/1997 | Bourke et al. | 424/489 |
| 5,656,295 A | 8/1997 | Oshlack et al. | 424/468 |
| 5,667,805 A | 9/1997 | Merrill et al. | 424/473 |
| 5,670,172 A | 9/1997 | Buxton et al. | 424/495 |
| 5,672,360 A | 9/1997 | Sackler et al. | 424/490 |
| 5,681,585 A | 10/1997 | Oshlack et al. | 424/494 |
| 5,811,126 A | 9/1998 | Krishnamurthy | 424/498 |
| 5,843,480 A | 12/1998 | Miller et al. | 424/484 |
| 5,849,240 A | 12/1998 | Miller et al. | 264/460 |
| 5,879,705 A | 3/1999 | Heafield et al. | 424/464 |
| 5,891,471 A | 4/1999 | Miller et al. | 424/468 |
| 5,914,131 A | 6/1999 | Merrill et al. | |
| 5,948,787 A | 9/1999 | Merrill et al. | 514/282 |
| 5,958,452 A | 9/1999 | Oshlack et al. | 424/457 |
| 5,958,459 A | 9/1999 | Chasin et al. | 424/490 |
| 5,965,163 A | 10/1999 | Miller et al. | 424/468 |
| 5,968,551 A * | 10/1999 | Oshlack et al. | 424/456 |
| 6,103,261 A | 8/2000 | Chasin et al. | 424/459 |
| 6,143,322 A | 11/2000 | Sackler et al. | 424/459 |
| 6,245,357 B1 | 6/2001 | Edgren et al. | |
| 6,261,599 B1 | 7/2001 | Oshlack et al. | 424/457 |
| 6,294,195 B1 | 9/2001 | Oshlack et al. | 424/457 |
| 6,419,960 B1 | 7/2002 | Krishnamurthy et al. | 424/490 |
| 6,733,783 B2 * | 5/2004 | Oshlack et al. | 424/473 |
| 7,514,100 B2 * | 4/2009 | Oshlack et al. | 424/473 |
| 2003/0224051 A1 | 12/2003 | Fink et al. | |
| 2004/0010000 A1 | 1/2004 | Ayer et al. | |
| 2005/0106249 A1 | 5/2005 | Hwang et al. | |

FOREIGN PATENT DOCUMENTS

| | | |
|---|---|---|
| EP | 0235986 B1 | 2/1987 |
| EP | 0235986 B2 | 2/1987 |
| EP | 0253104 B1 | 5/1987 |
| EP | 0235986 A1 | 9/1987 |
| EP | 0271193 A2 | 10/1987 |
| EP | 0271193 A3 | 10/1987 |
| EP | 0 253 104 | 1/1988 |
| EP | 0253104 A1 | 1/1988 |
| EP | 0267702 A3 | 5/1988 |
| EP | 0271193 B1 | 6/1988 |
| EP | 0327295 A2 | 8/1989 |
| EP | 0377518 A2 | 1/1990 |
| EP | 0377518 A3 | 1/1990 |
| EP | 0388954 A2 | 3/1990 |
| EP | 0388954 A3 | 3/1990 |
| EP | 0388954 B1 | 3/1990 |
| EP | 0361910 A1 | 4/1990 |
| EP | 0377517 A2 | 7/1990 |
| EP | 0377518 B1 | 7/1990 |
| EP | 0415693 A1 | 3/1991 |
| EP | 0452145 A2 | 10/1991 |
| EP | 0534628 B1 | 4/1992 |
| EP | 0532348 A3 | 9/1992 |
| EP | 0532348 B1 | 9/1992 |
| EP | 0576643 | 11/1992 |
| EP | 0532348 A2 | 3/1993 |
| EP | 0533297 A1 | 3/1993 |
| EP | 0534628 A1 | 3/1993 |
| EP | 0535841 A1 | 4/1993 |
| EP | 0546676 A1 | 6/1993 |
| EP | 0548448 A1 | 6/1993 |
| EP | 0553392 A1 | 8/1993 |
| EP | 0580860 A1 | 2/1994 |
| EP | 0636370 B1 | 6/1994 |
| EP | 0361680 B1 | 7/1994 |
| EP | 0609961 A1 | 8/1994 |
| EP | 0430287 B1 | 10/1994 |
| EP | 0636370 A1 | 2/1995 |
| EP | 0665010 A1 | 8/1995 |
| EP | 1258246 A2 | 11/2002 |
| GB | 2053681 B | 4/1984 |
| GB | 2170104 A | 7/1986 |
| GB | 2178313 A | 2/1987 |
| GB | 2196848 A | 5/1988 |
| JP | 5279245 | 4/1992 |
| WO | 80/00659 | 9/1979 |
| WO | 92/01446 | 2/1992 |
| WO | 92/02209 | 2/1992 |
| WO | 92/06679 | 4/1992 |
| WO | 92/08459 | 5/1992 |
| WO | 93/04675 | 3/1993 |
| WO | 93/07859 | 4/1993 |
| WO | 93/07861 | 4/1993 |
| WO | 93/10765 | 6/1993 |
| WO | 93/18753 | 9/1993 |
| WO | 94/03160 | 2/1994 |
| WO | 94/03161 | 2/1994 |
| WO | 94/05262 | 3/1994 |
| WO | 94/22431 | 10/1994 |
| WO | 9514460 | 1/1995 |
| WO | 95/14460 | 6/1995 |
| WO | 96/00066 | 1/1996 |
| WO | 96/01629 | 1/1996 |
| WO | 96/14058 | 5/1996 |
| WO | 9733566 | 9/1997 |
| WO | 9920255 | 4/1999 |
| WO | 01/08661 A2 | 7/2000 |
| WO | 02/100382 A2 | 12/2002 |
| WO | 03/004030 A1 | 1/2003 |
| WO | 03092648 | 3/2003 |
| WO | WO 2005/041968 | 5/2005 |

OTHER PUBLICATIONS

Agabeyoglu, I. and A. O. Ecz Fak, *Studies on Sustained Release II: In Vivo Performance of the Inert Matrix Sulfamethizole Tablet, Employing Polymethylmethacrylate*, 12 (3) Drug Development & Industrial Pharmacy 423-430 (1986).

Arkinstall, W. et al., *Efficacy of controlled-release codeine in chronic non-malignant pain: a randomized, placebo-controlled clinical trial*, 62 Pain 169-178 (1995).

Balant, L.P. and Gex-Fabry, M., Oral Controlled Release Products: Therapeutic and Biopharmaceutic Assessment, *Ch II. Controlled Release Products—Pharmacokinetic Aspects*, Gundert-Remy, U. and Möller, H. eds., Wissenschaftliche Verlagsgesellschaft mBH, Stuttgart at 21-37 (1990).

Bannerje, P.S. and Robinson, J.R., *Novel Drug Delivery Systems: An Overview of Their Impact on Clinical Pharmacokinetic Studies*, 20 (1) Clinical Pharmacokinetics 1-14 (1991).

Beaver, W.T. et al., *Analgesic Studies of Codeine and Oxycodone in Patients with Cancer. I. Comparisons of Oral with Intramuscular*

Codeine and of Oral with Intramuscular Oxycodone, 207 J. Pharmacology & Experimental Therapeutics 92-100 (1978).

Beaver, W.T. et al., *Analgesic Studies of Codeine and Oxycodone in Patients with Cancer. II. Comparisons of Intramuscular Oxycodone with Intramuscular Morphine and Codeine*, 207 J. Pharmacology & Experimental Therapeutics 101-108 (1978).

Beckett, A.H., Rate Control in Drug Therapy, Ch. 17: Once daily rate-controlled drug therapy, Prescott, L.F. and Nimmo, W.S. eds., Churchill Livingstone, Edinburgh at 166-179 (1985).

Benziger, D.P. et al., *A Pharmacokinetic/Pharmacodynamic Study of Controlled Release Oxycodone*, 13 (2) J. Pain & Symptom Management 75-82 (1997).

Bobs, G. et al., *Steady-State Pharmacokinetics of Sustained Release Morphine Tablets (MS Contin) and Morphine Sulfate Solution (MSS)*, 6 Proceedings of ASCO 44 Abstract #171 (1987).

Bourget, P. et al., *Study of the bioequivalence of two controlled-release formulations of morphine*, 33 (11) International J. Clinical Pharmacology & Therapeutics 588-94 (1995).

Brooks, I.M. et al., *Continuous Release Morphine Sulfate (CRMS) Tablets in Cancer Patients (pts) with Chronic Pain*, 5 Proceedings of ASCO 251 Abstract #980 (1986).

Brooks, I.M. et al., *Use of Continuous Release Morphine Sulfate (CRMS) in Cancer Patients with Chronic Pain*, 6 Proceedings of ASCO 264 Abstract #1037 (1987).

Brooks, J. et al., *Principles of Cancer Pain Management: Use of Long-acting Oral Morphine*, 28 (3) J. Family Practice 275-280 (1989).

Bruera, E. et al., *A Randomized, Double-Blind, Double-Dummy, Crossover Trial Comparing the Safety and Efficacy of Oral Sustained-Release Hydromorphone With Immediate-Release Hydromorphone in Patients with Cancer Pain*, 14 (5) J. Clinical Oncology 1713-1717 (1996).

Bruera, E. et al., *Randomized, Double-Blind, Cross-Over Trial Comparing Safety and Efficacy of Oral Controlled-Release Oxycodone With Controlled-Release Morphine in Patients With Cancer Pain*, 16 (10) J. Clinical Oncology 3222-3229 (1998).

Chary, S. et al., *The Dose-Response Relationship of Controlled Release Codeine (Codeine Contin) in Chronic Cancer Pain*, 9(6) J. Pain & Symptom Management 363-371 (1994).

Chmielewski, D.H. et al., *Comparative Bioavailability of Multiple Doses of Sustained Release Morphine Tablets (Rosanol SR q 12h) and Immediate Release Morphine Solution (q 4h)*, 6 Proceedings of ASCO 275 Abstract #1080 (1987).

Citron, M.L. et al., *Long-Term Administration of Controlled-Release Oxycodone Tablets for the Treatment of Cancer Pain*, 16(8) Cancer Investigation 562-571 (1998).

Comerford, T., *Efficacy of Controlled-Release Oxycodone*, Letters to the Editor, 17 (2) J. Clinical Oncology 738 (1999).

Cowan, D.A. et al., *Two Assays for Dihydrocodeine in Plasma and in Urine and Their Use to Determine the Bioavailability of a Controlled-Release Product*, 77 (7) J. Pharmaceutical Sciences 606-609 (1988).

Cundiff, D. et al., *Evaluation of a Cancer Pain Model for the Testing of Long-Acting Analgesics: The Effect of MS Contin in a Double-Blind, Randomized Crossover Design*, 63 (11) Cancer Jun. 1 Supplement 2355-2359 (1989).

Curtis, G.B. et al., *Relative Potency of Controlled-Release Oxycodone and Controlled-Release Morphine in Postoperative Pain Model*, 55 European J. Clinical Pharmacology 425-429 (1999).

Deschamps, M. et al., *The Evaluation of analgesic effects in cancer patients as exemplified by a Double-Blind, Crossover Study of Immediate-Release versus Controlled-Release Morphine*, 7 (7) J. Pain Symptom Management 384-392 (1992).

Dhaliwal, H.S. et al., *Randomized Evaluation of Controlled-Release Codeine and Placebo in Chronic Cancer Pain*, 10 (8) J. Pain & Symptom Management 612-623 (1995).

DiPersio, D.M. and Moses, S.S., *Predicting plasma procainamide concentrations resulting from a sustained release preparation*, 4 Clinical Pharmacy 186-191 (1985).

Esterhail, J.L. et al., *Post operative analgesic efficacy of controlled release morphine*, Abstract, Pain (Suppl. 4) S230 (1987).

Finn, J.W. et al., *Crossover Study of Sustained Release Morphine Sulfate (Roxanol SR) in Advanced Cancer*, 6 Proceedings of ASCO 44 Abstract #1027 (1987).

Finn, J.W., *Placebo-Blinded Study of Morphine Sulfate Sustained-Release Tablets and Immediate-Release Morphine Sulfate Solution in Outpatients With Chronic Pain Due to Advanced Cancer*, 11 (5) Clinical Oncology 967-972 (1993).

Fitzmartin, R.D. and Reder, R.F., *Stigma associated with opioid therapy for pain, results of a health care provider survey*, American Pain Society, 14th annual Scientific Meeting, A144 abstract #95877, Nov. 9-12 (1995).

Foley K.M., *The Treatment of Cancer Pain*, 313 New England J. Medicine 84-95 (1985).

Gibaldi, M. and Perrier, D., Pharmacokinetics, 2nd Ed., Rev. & Exp., Marcel Dekker, Inc., New York at 456-457; 353-357 (1982).

Gibaldi, M. and Perrier, D., Pharmacokinetics, Ch. 4: Absorption Kinetics and Bioavailability, 2nd Ed., Rev. & Exp., Marcel Dekker Inc., New York at 145-198 (1985).

Glare, P.A. and Walsh, D., *Oxycodone—a substitute for morphine in cancer pain management?* 6 Palliative Medicine 79-80 (1992).

Gostick, N. et al., *A comparison of the efficacy and adverse effects of controlled release dihydrocodeine and immediate release dihydrocodeine in the treatment of pain in osteoarthritis and chronic back pain*, The Edinburgh Symposium on Pain Control and Medical Education (R. G. Twycross, ed.), Royal Society of Medicine Services International Congress and Symposium Series No. 149, London, 137-143 (1989).

Grandy, R. et al., *Bioavailability Comparison of Three Controlled-Release Codeine Formulations vs. Conventional Oral Codeine*, 3 (3) J. Pain & Symptom Management Abstract S17 #27 (1988).

Grass, G.M. and Robinson, J.R., Modern Pharmaceutics, Ch. 16: Sustained and Controlled-Release Drug Delivery Systems, 2nd Ed., Marcel Dekker, Inc., New York at 635-671 (1989).

Hagen, N. A. and Babul, N., *Comparative clinical efficacy and safety of a novel controlled-release oxycodone formulation and controlled-release hydromorphone in the treatment of cancer pain*, 79 (7) Cancer 1428-37 (1997).

Hale, M.E. et al., *Efficacy and Safety of Controlled-Release Versus Immediate-Release Oxycodone: Randomized, Double-Blind Evaluation in Patients with Chronic Back Pain*, 15 Clinical. J. Pain 179-183 (1999).

Hanks, G.W., *Controlled-Release Morphine (MST Contin) In Advanced Cancer The European Experience*, 63 (11) Cancer Jun. 1 Supplement 2378-2382 (1989).

Hays, H. et al., *Comparative Clinical Efficacy and Safety of Immediate Release and Controlled Release Hydromorphone for Chronic Severe Cancer Pain*, 74 (6) Cancer 1808-1816 (1994).

Heinrich-Nols, J. et al., *Bioequivalence study of two morphine extended release formulations after multiple dosing in healthy volunteers*, 37 (3) International J. Clinical Pharmacology & Therapeutics 153-158 (1999).

Heiskanen, T. and Kalso, E., *Controlled-Release Oxycodone and Morphine in Cancer Related Pain*, 73 Pain 37-45 (1997).

Heiskanen, T.E. et al., Morphine or Oxycodone in Cancer Pain?, 39 (8) Acta Oncologica 941-947 (2000).

Hood, G.M. et al., Dose and Effectiveness of Oral Oxycodone Following PCA Morphine for Post-Operative Analgesia, Abstracts 7th World Congress on Pain, 390, Abstract 1028, Poster # 14 (1993).

Houde, R.W. et al., Analgetics, Ch. III: Clinical Measurement of Pain, deStevens, G. ed., Academic Press, New York at 75-122(1965).

Houde, R.W., *The Use and Misuse of Narcotics in the Treatment of Chronic Pain*, 4 Advances in Neurology 527-536 (1974).

Houston, A.C. and Yeang, Y., *The Influence of food on the Pharmacokinetics of Morphine from Two controlled Release Preparations*, 2 British J. Clinical Research 201-209 (1991).

Hunt, T.L. and Kaiko, R.F., *Comparison of the Phramacokinetic Profiles of Two Oral Controlled-Release Morphine Formulations in Healthy Young Adults*, 13 (4) Clinical Therapeutics 482-488 (1991).

Jamison, R.N. and Ferrante, F.M., Survey of Opioid Use in Chronic Nonmalignant Pain Patients, 11th Annual Scientific Meeting, American Pain Society, Oct. 22, Abstract #92467 (1992).

Kaiko, R.F. et al., *Basics of Opioid Analgesic Pharmacodynamics*, 1 (2) J. Pain & Symptom Management 103-105 (1986).

Kaiko, R. et al., *Pharmacokinetic Characterization of Controlled-Release Oral Codeine for Chronic Cancer Pain*, 5 Proceedings of ASCO 255 #996 (1986).

Kaiko, R.F. et al., *Bioequivalency of controlled-release 60 mg morphine vs. two MS Contin 30 mg tablets*, Oncology Nursing Forum Suppl Mar.-Apr. 118, Abstract #148P (1987).

Kaiko, R.F. et al., *Bioequivalency of Controlled-Release 100 mg Morphine vs. Three Ms Contin 30 mg Tablets*, 6 Proceedings of ASCO 271 Abstract 1066 (1987).

Kaiko, R.F. et al., *The United States Experience With Oral Controlled-Release Morphine (MS Contin Tablets): Parts I and II. Review of Nine Dose Titration Studies and Clinical Pharmacology of 15mg, 30-mg, 60-mg, and 100-mg Tablet Strengths in Normal Subjects*, 63 (11) Cancer Jun. 1 Supplement 2348-2354 (1989).

Kaiko, R.F. et al., *Controlled-Release Morphine Bioavailability (MS Contin® Tablets) in the Presence and Absence of Food*, 6 (4) Hospice J. 17-30 (1990).

Kaiko, R. et al., *A single-dose study of the effect of food ingestion and timing of dose administration on the pharmacokinetic profile of 30-mg sustained-release morphine sulfate tablets*, 47 (5) Current Therapeutic Research 869-878 (1990).

Kaiko, R.F. et al., *Controlled-Release Oral Morphine (MS Contin Tablets, MSC) in Postoperative Pain*, 183 (6) European J. Pharmacology 1437-1438 (1990).

Kaiko, R.F., Controlled-Release Oral morphine for Cancer-Related Pain: The European and North American Experiences, Advances in Pain Research and Therapy, vol. 16 K.M. Foley, ed., Raven Press, Ltd., New York at 171-189 (1990).

Kaiko, R.F., *Relationship between opioid disposition and their pharmacological effects—an overview*, 67 (Suppl. 2) Postgraduate Medical J. S44-S49 (1991).

Kaiko, R.F. et al., *The Bioavailability of Morphine in Controlled-Release 30 mg Tablets per Rectum Compared With Immediate-Release 30-mg Rectal Suppositories and Controlled-Release 30-mg Oral Tablets*, 12 (2) Pharmacotherapy 107-113 (1992).

Kaiko, R.F. et al., *A Bioequivalence Study of Oral Controlled-Release Morphine Using Naltrexone Blockade*, 35 J. Clinical Pharmacology 499-504 (1995).

Kaiko, R. et al., *Analgesic Onset and Potency of Oral Controlled-Release (CR) Oxycodone and CR Morphine*, Clinical Pharmacology & Therapeutics, Abstract 130 #PI-4 (1996).

Kaiko, R. et al., *Steady-state Bioavailability Evaluation of Controlled Release Oral Codeine*, FASEB J. Abstract A1558 #7333 May 1-May 5 Meeting of the Federation of American Societies for Experimental Biology (72$^{nd}$ Annual Meeting, Las Vegas NV) (1998).

Kalso, E., Hallucinations during morphine but not during oxycodone treatment, 2 (8616) The Lancet 912 (1988).

Kalso, E. and Vainio, A., *Morphine and oxycodone hydrochoride in the management of cancer pain*, 47 (5) Clinical Pharmacology & Therapeutics 639-646 (1990).

Kalso, E. et al., *Morphine and Oxycodone in the Management of Cancer Pain: Plasma Levels Determined by Chemical and Radioreceptor Assays*, 67 Pharmacology & Toxicology 322-328 (1990).

Kalso, E. et al., *Intravenous morphine and oxycodone for pain after abdominal surgery*, 35 Acta Anaesthesiologica Scandinavica 642-646 (1991).

Kaplan, R. et al., *Comparison of Controlled-Release and Immediate Release Oxycodone Tablets in Patients with Cancer Pain*, 16 (10) J. Clinical Oncology 3230-3237 (1998).

Khan, M. Zahirul I., *Dissolution testing for sustained or controlled release oral dosage forms and correlation with in vivo data: challenges and opportunities*, 140 International J. of Pharmaceutics 131-143 (1996).

Khojasteh, A. et al., *Safety and Efficacy of Slow-Release Morphine Sulfate Tablets in Cancer Pain Therapy*, 5 Proceedings of ASCO 256 Abstract #1000 (1986).

Krant, M. et al., Cancer Pain Management with Controlled-Release Oral Morphine, 5 Proceedings of ASCO 251 Abstract #981 (1986).

Lapin, J. et al., *Cancer pain management with a controlled-release oral morphine preparation*, 4 (3) J. Pain & Symptom Management 146-151 (1989).

Lazarus, J. & Cooper, J., *Absorption, Testing, and Clinical Evaluation of Oral Prolonged-Action Drugs*, 50 (9) J. Pharmaceutical Sciences 715-732 (1961).

Leeson, L.J. et al., *The In Vitro Development of Ertended-Release Solid Oral Dosage Forms*, 13 (5) J. Pharmacokinetics & Biopharmaceutics 493-514 (1985).

Lehmann, K., *Acrylic Latices from Redispersable Powders for Peroral and Transdermal Drug Formulations*, 12 (3) Drug Development and Industrial Pharmacy 265-287 (1986).

Leow, K.P. et al., *Comparative Oxycodone Pharmacokinetics in Humans After Intravenous, Oral, and Rectal Administration*, 14 (6) Therapeutic Drug Monitoring 479-484 (1992).

Leow, K.P. et al., *Single-Dose and Steady-State Pharmacokinetics and Pharmacodynamics of Oxycodone in Patients With Cancer*, 52 Clinical Pharmacology & Therapeutics 487-495 (1992).

Leslie, S.T. et al., *Letters to the Editors: Controlled Release Morphine Sulphate Tablets—A Study in Normal Volunteers*, 9 British J. Clinical Pharamacology 531-534 (1980).

Leslie, S.T., *Continus Controlled Release Preparations*, Symposium Supplement 10 British J. Clinical Pharmacology 5-8 (1981).

Lloyd, R.S. et al., *The efficacy and tolerability of controlled-release dihydrocodeine tablets and combination dextropropoxyphene/paracetamol tablets in patients with severe osteoarthritis of the hips*, 13 (1) Current Medical Research Opinions 37-48 (1992).

LoRusso, P. et al., *Comparison of Controlled-release oxycodone (OxyContin™) tablets to controlled-release morphine (MS Contin®) in patients with cancer pain*, American Pain Society, 15$^{th}$ Annual Scientific Meeting, Abstract #675 (1996).

LoRusso, P. et al., *The Effects of Oral Controlled-Release Morphine and Oxycodone on Cancer-Related Neuropathic Pain*, American Pain Society: 17$^{th}$ Annual Scientific Meeting, Poster Abstracts 130 #724 (1998).

MacDonald, N. et al., *A Double-Blind, Cross-Over Comparison Between Slow-Release Morphine (SRM) and Short-Acting Morphine (SAM) in the Treatment of Cancer Pain*, 6 Proceedings of ASCO 44 Abstract #1054 (1987).

Mandema, J.W. et al., *Pharmacokinetic Model For A New Oral Controlled Release Formulation Of Oxycodone*, 81 (3A) Anesthesiology A383 (1994).

Mucci-LoRusso, P. et al, *Controlled-release oxycodone compared with controlled-release morphine in the treatment of cancer pain: a randomized, double-blind, parallel-group study*, 2 European J. Pain 239-249 (1998).

Paul, D. et al., *Pharmacological Characterization of Morphine-6-Beta-Glucuronide, a very potent morphine metabolite*, 251 (2) J. Pharmacology & Experimental Therapeutics 477-483 (1989).

Physician's Desk Reference, OxyContin, 56 Ed. at 2912-2916, (2002).

Portenoy, R.K. et al., *Oral Controlled-Release Morphine Sulfate, Analgesic Efficacy and Side Effects of a 100-mg Tablet in Cancer Pain Patients*, 63 Cancer Jun. 1 Supplement 2284-2288 (1989).

Portenoy, R.K. and Coyle, N., *Controversies In The Long-Term Management Of Analgesic Therapy In Patients With Advanced Cancer*, 5 (5) J. Pain & Symptom Management 307-319 (1990).

Portenoy, R.K. et al., *The Metabolite Morphine 6-glucuronide Contributes to the Analgesia Produced by Morphine Infusion in Patients with Pain and Normal Renal Function*, 51 (4) Clinical Pharmacology & Therapeutics 422-431 (1992).

Poyhia, R. et al., *The Pharmacokinetics of oxycodone after intravenous injection in adults*, 32 British J. Clinical Pharmacology 516-518 (1991).

Poyhia, R. et al., *The pharmacokinetics and metabolism of oxycodone after intramuscular and oral administration to healthy subjects*, 33 (6) British J. Clinical Pharmacology 617-621 (1992).

Poyhia, R. et al., *A Review of Oxycodone's Clinical Pharmacokinetics and Pharmacodynamics*, 8 (2) J. Pain & Symptom Management 63-67 (1993).

Reder, R.F. and Fitzmartin, R.D., *Physician Survey of Attitudes About Controlled-Release Oxycodone (OXYCR)*, American Pain Society, 14$^{th}$ Annual Scientific Meeting A144 Abstract #95878 Nov. 9-12 (1995).

Reder, R. et al., Ease of Titration to Stable Pain Control in Chronic Pain Patients with Controlled-Release Oral Oxycodone (OxyContin™) Tablets, Abstracts, 8th World Congress on Pain, Vancouver, Canada, Aug. 17-22, 53 Abstract #171, (1996).

Reder, R.F. et al., *Steady-State Bioavailability of Controlled-Release Oxycodone in Normal Subjects*, 18 (1) Clinical Therapeutics 95-105 (1996).

Renzi, N. L. and Tam, J.N., *Quantitative GLC Determination of Oxycodone in Human Plasma*, 68 (1) J. Pharmaceutical Sciences 43-45 (1979).

Riegelman, S. and Collier, P., *The application of statistical moment theory to the evaluation of in vivo dissolution time and absorbtion time*, 8 (5) J. Pharmacokinetics & Biopharmaceutics 509-534 (1980).

Robinson, J.R. and Eriksen, S.P., *Theoretical formulation of sustained-release dosage forms*, 55 (11) J. Pharmaceutical Sciences 1254-1263 (1966).

Robinson, J.R. and Eriksen, S.P., *Theoretical approach to sustained-release multiple-dose therapy: noncumulative attainment of desired blood level*, 59 (12) J. Pharmaceutical Sciences 1796-1800 (1970).

Rodda, B.E., *Sustained Release Preparations: Estimation of Plasma Concentration in the One Compartment Open Model when Release is both Immediate and Zero Order*, 194 Archives Internationales De Pharmacodynamic Et De Therapie 290-296 (1971).

Rogers, A.G., *The Underutilization of Oxycodone*, 6 (7) J. Pain & Symptom Management 452 (1991).

Salzman, R.F. et al., *Can a Controlled-Release Oral Dose Form of Oxycodone Be Used as Readily as an Immediate-Release Form For the Purpose of Titrating to Stable Pain Control?*, 18 (4) J. Pain & Symptom Management 271-279 (1999).

Savarese, J.J. et al., *Steady-State Pharmacokinetics of Controlled Release Oral Morphine Sulphate in Healthy Subjects*, 11 Clinical Pharmacokinetics 505-510 (1986).

Savarese, J. et al., *Controlled-Release Oral Morphine Sulfate (MS Contin®), A Twelve Hour Analgesic Confirmed by Rescue Factor Design*, 6 Proceedings of ASCO 264 Abstract #1038 (1987).

Sawe, J. et al., *Morphine kinetics in cancer patients*, 30 (5) Clinical Pharmacology & Therapeutics 629-635 (1981).

Steinbach, D. et al., *Evaluation of Pharmaceutical Availability from the Calculation of Drug Levels and Release Profiles*, 4 International J. of Pharmaceutics 327-335 (1980).

Stelmach, H. et al., *Release of a Drug from a Dosage Form*, 54 (10) J. Pharmaceutical Sciences 1453-1458 (1965).

Sun, H. and Moses, S.S. Chow, *A Method of Determining the In Vivo Drug Release Rate Constant of Sustained-Release Preparation*, 23 (4) Drug Metabolism and Disposition 449-454 (1995).

Sunshine, A. et al., *Analgesic Effects of Oral Oxycodone and Codeine in the Treatment of Patients with Postoperative, Postfracture, or Somatic Pain*, 8 Advances Pain Research Therapy, Foley, K.M. and Inturrisi, C.E. eds., Raven Press, New York 225-235 (1986).

Sunshine, A. et al., *Analgesic Efficacy of Controlled-Release Oxycodone vs. Immediate-Release Oxycodone Alone and in Combination with Acetaminophen in Postoperative Pain: A Preliminary Study, Problems of Drug Dependence*, 1992: Proceeding of the 54th Annual Scientific Meeting, U.S. Department of Health and Human Services, 329 (1992).

Sunshine, A. et al., *Controlled-Release Oxycodone vs. Immediate Release Oxycodone Alone and in Combination with Acetaminophen in the Treatment of Postoperative Pain*, 11th Annual Scientific Meeting, American Pain Society, Oct. 22, Abstract #92466 (1992).

Sunshine, A. et al., *Onset And Duration Of Analgesia For Controlled Release Vs. Immediate Release Oxycodone Alone and In Combination With Acetaminophen In Postoperative Pain*, 57 (2) Clinical Pharmacology & Therapeutics 137 Abstract #PI-7 (1995).

Sunshine, A. et al., *Analgesic Efficacy of Controlled-Release Oxycodone in Postoperative Pain*, 36 (7) J. Clinical Pharmacology 595-603 (1996).

Thirlwell, M.P. et al., *Pharmacokinetics and Clinical Efficacy of Oral Morphine Solution and Controlled-Release Morphone Tablets in Cancer Patients*, 63 (11) Cancer Jun. 1 Supplement 2275-2283 (1989).

Wagner, J., *Biopharmaceutics: 23: Rate of Dissolution In Vitro and In Vivo: Part VIII. Examples of Quantitative Correlations of in Vivo with in Vitro Data*, 4 Drug Intelligence and Clinical Pharmacy 232-239 (1970).

Wagner, J., Biopharmaceutics, *Ch. 21: Quantitative Correlations of in Vivo Data with in Vitro Rate of Dissolution Data*, 1st ed., Drug Intelligence Publications, Illinois at 140-147 (1971).

Walsh, T.D. et al., *Disposition of Oral Morphine in Advanced Cancer*, 6 Proceedings of ASCO 270 Abstract #1063 (1987).

Welling, P.G. and Dobrinska, M.R., Sustained and Controlled Release Drug Delivery Systems, *Ch. 9: Multiple Dosing of Sustained Release Systems*, J.R. Robinson, ed., Marcel Dekker, Inc., New York at 631-716 (1978).

Welling, P.G., Pharmaceutical Bioequivalence—*Ch. 8*—In Vitro Methods to Determine Bioavailability: In Vitro-In Vivo Correlations, Marcel Dekker, Inc., New York at 223-232 (1991).

Wiegand, R.G. and Taylor, J.D., *Kinetics of Plasma Drug Levels after Sustained Release Dosage*, 3 Biochemical Pharmacology 256-263 (1960).

Wilson, A.B and Draffan, G.H., Rate Control in Drug Therapy, Ch. 4: Implications of Toxicology, Prescott, L.F. and Nimmo, W.S. eds., Churchill Livingstone, Edinburgh at 30-37 (1985).

Wotherspoon, H.A. et al., *Analgesic efficacy of controlled-release dihydrocodeine: A comparison of 60, 90 and 120 mg tablets in cold-induced pain*, 46 Anaesthesia 915-917 (1991).

The Merck Index, 11th ed., Budavari, S. ed., at pp. 384-385, 500, 762, 988, and 1100 (1989).

Federal District Court Decision, *Purdue Pharma, L.P.*, v. *Boehringer Ingelheim GmbH*, 98 F. Supp. 2d. 362; 2000, U.S. Dist., S.D.N.Y.; U.S.P.Q. 2D 1168, Judge Sidney Stein decided May 16, 2000.

Federal Court of Appeals Decision, *Purdue Pharma, L.P.*, v. *Boehringer Ingelheim GmbH*, Docket No. 00-1398, Judge Sidney Stein, decided Feb. 1, 2001.

Purdue's Proposed Findings Of Fact And Conclusions Of Law After Trial in *Purdue Pharma L.P., The Purdue Frederick Company, The P.F. Laboratories, Inc., The Purdue Pharma Company* (*Plaintiffs and Counterclaim Defendents*) v. *Endo Pharmaceuticals, Inc.* (*Defendant and Counterclaim Plaintiff*), *Endo Pharmaceuticals Holdings, Inc.* (*Defendant*) v. *EuroCeltique S.A.*(*Counterclaim Defendant*) Civil Action Nos. 00-Civ. 8029 (SHS); 01-Civ. 2109 (SHS); Civil Action Nos. 01-Civ. 8117 (SHS).

Prosecution File History, U.S. Patent No. 4,861,598, filed Jul. 18, 1986.

Abstract of Japan, XP-002241447, May 12, 1988.

Abstracts from the Twelfth Annual Congress of the Oncology Nursing Society, May 1987.

Advertisement: MS Contin 1986, 1987 The Purdue Frederick Company.

Advertisement: Roxanol SR., 1988 Roxane Labs, Inc.

Beubler, E., "Medikamentose Schmerztherapie: Kriterien, Moglichkeiten, Risken," *Therapiewoche Osterreich*, 7, 2 (1992), pp. 1-15, English translation.

Bloomfield, MD, Saul S., et al., "Analgesic efficacy and potency of two oral controlled release morphine preparations", Clin. Pharm & Therapeutics, vol. 53, No. 4 (1993) pp. 469-478.

Flanders, P., et al., "The Control of Drug Release From Conventional Melt Granulation Matrices," *Drug Development and Industrial Pharmacy*, vol. 13, No. 6, pp. 1001-1022 (1987).

Gourlay, Geoffrey K., Ph.D., et al., "Influence of a high-fat meal on the absorption of morphine from oral solutions, " *Clin. Pharmacol. Ther.*, Oct. 1989, pp. 463-468.

Gourlay, Geoffrey K., Ph.D., Ph.D., "The Reproducibility of Bioavailability of Oral Morphine from Solution Under Fed and Fasted Conditions," *Journal of Pain and Sympton Management*, vol. 6., No. 7, Oct. 1991, pp. 431-436.

Kaiko, R.F. "The Pre-and Postoperative Use of Controlled-Release Morphine (MS Contin Tablets): A Review of the Published Literature" Medical Department, The Purdue Frederick Company, Royal Society of Medical Services, International Congress, Symposium Services, No. 149, pp. 147-160 (1989).

Kaiko, R.F. "Clinical Protocol and Role of Controlled Release Morphine in the Surgical Patient" Anesthesiology and Pain Management 1991 pp. 193-212.

Lapin, J., et al., "Guidelines for use of Controlled Release Oral Morphine in Cancer pain Management," *Cancer Nursing*, v 12 (4), pp. 202-8, 1989.

McTaggart, Celia M., et al., "The evaluation of formulation and processing conditions of a melt granulation process," *International Journal of Pharmaceutics*, vol. 19, pp. 139-148 (1984).

Munday, D.L., "Changes in Drug Release Rate 2, Effect of Temperature and Relative Humidity on Polymeric Film Coatings," *5th Cong. Int. Tech. Pharm.*, 1989, vol. 2, pp. 55-60.

Physicians Desk Reference 1994, 48th Edition, pp. 1821-1824.

Schaefer, T., et al., "Melt granulation in a laboratory scale high shear mixer," *Drug Development and Industrial Pharmacy*, vol. 16, No. 8, pp. 1249-1277 (1990).

Slowey, H.F., et al., "Effect of Premedication with Controlled-Release Oral Morphine on Postoperative Pain," Anaesthesia, 1985, vol. 40, pp. 438-440.

Sunshine, Abraham et al., "Analgesic oral efficacy of tramadol hydrochloride in postoperative pain," *Clin. Pharmacol. Ther.*, Jun. 1992, pp. 740-746.

Sustained Release Medications, Noyes Data Corp., pp. 3,4, 10-15, 96-99, 335-337 (1980).

Thomsen, L. Juul, "Utilizing melt pelletization technique for the preparation of prolonged release products," *Pelletization*, (material elaborated by assistant prof. Lars Juul Thomsen, Department of Pharmaceutics, Royal Danish School of Pharmacy for the DIE course "Pelletization Technologh," Nov. 1992, 106 pages plus 3 appendices.

Thomsen, L. Juul, et al., "Prolonged Release Matrix Pellets Prepared by Melt Pelletization I. Process Variables," *Drug Development and Industrial Pharmacy*, vol. 19, No. 15, pp. 1867-1887 (1993).

Thomsen, L.. Juul, "Prolonged Release Matrix Pellets Prepared by Melt Pelletization. Part IV: Drug Particles Size, and Binder Composition," *Pharmaceutical Technology Europa*, pp. 19-24 (Oct. 1994).

Yokokawa, N., et al., "Relationship between plasma concentration of morphine and analgesic effectiveness," *Postgrad Med J*, (1991) 67 (Suppl. 2) pp. S50-S54.

Extended European Search Report issued in connection with corresponding European Application No. 08151238.6 on Mar. 23, 2010.

\* cited by examiner

US 7,846,476 B2

ONCE-A-DAY OXYCODONE FORMULATIONS

This application is a 371 of PCT/US02/14024, which claims the benefit of U.S. Provisional Application No. 60/288,211, filed May 2, 2001, the disclosure of which is hereby incorporated by reference.

FIELD OF THE INVENTION

The invention is directed to sustained release formulations containing oxycodone or a pharmaceutically acceptable salt thereof which is suitable for administration to a patient.

BACKGROUND OF THE INVENTION

Once-a-day sustained release opioid formulations are disclosed in U.S. Pat. Nos. 5,478,577; 5,672,360; 5,958,459; 6,103,261; 6,143,332; 5,965,161; 5,958,452 and 5,968,551. All documents cited herein, including the foregoing, are incorporated by reference in their entireties for all purposes.

SUMMARY AND OBJECTS OF THE INVENTION

It is an object of the present invention to provide an oxycodone formulation suitable for once daily administration for effective pain management.

It is an object of preferred embodiments of the present invention to provide a pharmaceutically acceptable dosage form for orally administering oxycodone to provide analgesic therapy beyond its relatively short half-life over an extended period of time, and having a duration of pain relief of at least 24-hours.

The above objects and others are attained by the present invention, which is directed to a dosage form comprising an analgesically effective amount of oxycodone or a pharmaceutically acceptable salt thereof and a sustained release material, the dosage form providing an analgesic effect for at least about 24 hours after oral administration at steady state to human patients; and the dosage form providing a mean $C_{24}/C_{max}$ oxycodone ratio of 0.6 to 1.0 after oral administration at steady state to the patients.

In certain embodiments of the invention, the dosage form after administration to patients provides a mean $T_{max}$ of oxycodone in-vivo which occurs at about 2 to about 17 hours (e.g., about 2 to about 8 hours) after administration at steady state of the dosage form.

In certain embodiments of the invention, the mean $T_{max}$ of oxycodone in-vivo occurs at about 6.5 hours to about 17 hours, at about 8 to about 16 hours, at about 10 to about 16 hours, or at about 12 to about 16 hours after administration at steady state of the dosage form.

In certain embodiments of the invention, the dosage form provides an analgesic effect for at least about 24 hours after administration of the dosage form to human patients at steady state; and provides a mean $C_{24}/C_{max}$ oxycodone ratio of 0.60 to 1.0 after administration at steady state to patients.

In certain embodiments of the invention, the dosage form provides an analgesic effect for at least about 24 hours after administration at steady state to human patients; and provides a mean $C_{24}/C_{max}$ oxycodone ratio of 0.60 to 1.0 or 0.7 to 1.0 after administration at steady state to patients. In certain embodiments of the invention, the dosage form provides an in-vitro release rate, of oxycodone or a pharmaceutically acceptable salt thereof, when measured by the USP Basket Method at 100 rpm in 900 ml aqueous buffer at a pH of between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours.

In certain preferred embodiments the sustained release oral dosage form of the present invention provides oxycodone plasma levels which are effective for 24 hourly dosing, characterized by a $W_{50}$ for the oxycodone of between 4 and 24 hours after administration at steady state. In certain embodiments, the $W_{50}$ is at least 4 hours, preferably at least 12 hours, and more preferably at least 18 hours, after administration at steady state.

In certain embodiments the sustained release oral dosage form of the present invention comprises a matrix which includes a sustained release material and oxycodone or a pharmaceutically acceptable salt thereof. In certain embodiments, the matrix is compressed into a tablet and may be optionally overcoated with a coating that in addition to the sustained release material of the matrix may control the release of the oxycodone or pharmaceutically acceptable salt thereof from the formulation, such that blood levels of active ingredient are maintained within the therapeutic range over an extended period of time. In certain alternate embodiments, the matrix is encapsulated.

In certain embodiments, the sustained release oral dosage form of the present invention comprises a plurality of pharmaceutically acceptable sustained release matrices comprising oxycodone or a pharmaceutically acceptable salt thereof, the dosage form maintaining the blood plasma levels of oxycodone within the therapeutic range over an extended period of time when administered to patients.

Preferably, the formulations prepared in accordance with the present invention can be presented in tablet, capsule, or in any other suitable unit dosage form.

In certain embodiments the sustained release oral dosage form of the present invention is an osmotic dosage form which comprises a single layer or bilayer core comprising oxycodone or a pharmaceutically acceptable salt thereof; an expandable polymer; a semipermeable membrane surrounding the core; and a passageway disposed in the semipermeable membrane for sustained release of the oxycodone or pharmaceutically acceptable salt thereof, such that blood levels of active ingredient are maintained within the therapeutic range over an extended period of time when administered to patients.

In certain embodiments the sustained release oral dosage form of the present invention comprises a substantially homogenous core comprising oxycodone or a pharmaceutically acceptable salt thereof and an expandable polymer; a semipermeable membrane surrounding the core; and a passageway disposed in the semipermeable membrane for sustained release of the oxycodone or pharmaceutically acceptable salt thereof, such that blood levels of active ingredient are maintained within the therapeutic range over an extended period of time when administered to a patients.

In certain embodiments of the present invention, there is provided a method of treating pain associated conditions in patients requiring such treatment which method includes administering to a patient an effective amount of oxycodone or a pharmaceutically acceptable salt thereof in a sustained release dosage form as described herein.

In certain embodiments, the invention is directed to the use of a sustained release dosage form comprising a pharmaceutically acceptable matrix comprising oxycodone or a pharmaceutically acceptable salt thereof and a sustained release material in the production of an analgesic preparation for oral administration to human patients on a once a day basis, to provide an analgesic effect for at least about 24 hours and a mean $C_{24}/C_{max}$ oxycodone ratio of 0.6 to 1.0 after administration at steady state to said patients.

In certain embodiments, the invention is directed to the use of a sustained release oral dosage form comprising a bilayer core comprising a drug layer comprising an analgesically effective amount of oxycodone or a pharmaceutically acceptable salt thereof; and a displacement layer comprising an osmopolymer; and a semipermeable wall surrounding the bilayer core having a passageway disposed therein for the release of said oxycodone or pharmaceutically acceptable salt thereof; in the production of an analgesic preparation for oral administration to human patients to provide an analgesic effect at least about 24 hours after oral administration at steady state to human patients; and to provide a mean $C_{24}/C_{max}$ oxycodone ratio of 0.6 to 1.0 after administration at steady state to said patients.

In certain embodiments, the invention is directed to the use of a sustained release dosage form comprising a plurality of sustained release matrices comprising oxycodone or a pharmaceutically acceptable salt thereof and a sustained release material, in the production of an analgesic preparation for oral administration to a patient on a once-a-day basis, to provide an analgesic effect for at least 24 hours after oral administration at steady state to human patients; and to provide a mean $C_{24}/C_{max}$ oxycodone ration of 0.6 to 1.0 after oral administration at steady state to said patients.

The term "$C_{max}$" as it is used herein is the highest plasma concentration of the drug attained within the dosing interval.

The term "$C_{24}$" as it is used herein is the plasma concentration of the drug at 24 hours after administration.

The term "$T_{max}$" as it is used herein is the time period which elapses after administration of the dosage form until the plasma concentration of the drug attains the highest plasma concentration within the dosing interval.

The term "$W_{50}$" for purposes of the present invention is the duration over which the plasma concentrations are equal to or greater than 50% of the peak concentration. The parameter is determined by linear interpolation of the observed data and represents the difference in time between the first (or only) upslope crossing and the last (or only) downslope crossing in the plasma profile.

The term "$C_{24}/C_{max}$ ratio" is defined for purposes of the present invention as the ratio of the plasma concentration of the drug at 24 hours after administration to the highest plasma concentration of the drug attained within the dosing interval.

The term "USP Basket Method" is the Basket Method described in U.S. Pharmacopoeia XXII (1990), herein incorporated by reference.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

The term "semipermeable wall" for purposes of the present invention means that the wall is permeable to the passage of an exterior fluid, such as aqueous or biological fluid, in the environment of use, including the gastrointestinal tract, but impermeable to drug.

The term "expandable polymer" for purposes of the present invention means a polymer which upon exposure to an aqueous or biological fluid, absorbs the fluid resulting in a greater mass.

The term "mean" for purposes of the present invention, when used to define a pharmacokinetic value (e.g., $T_{max}$) represents the arithmetic mean value measured across a patient population.

The phrase "pharmaceutically acceptable salt" includes, but is not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, fumarate, tartrate and the like; sulfonates such as methanesulfonate, benzenesulfonate, p-toluenesulfonate, and the like; amino acid salts such as arginate, asparginate, glutamate and the like.

DESCRIPTION OF THE INVENTION

In certain embodiments of the present invention, the sustained release dosage form provides an in-vitro release rate of oxycodone or a pharmaceutically acceptable salt thereof, when measured by the USP Basket Method at 100 rpm in 900 ml aqueous buffer at a pH of between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hrs, and greater than about 50% at 24 hours.

In certain embodiments of the present invention the time period during which oxycodone blood levels (after administration at steady state) are greater than or equal to 75% of the maximum blood level ($T_{\geq 0.75 Cmax}$) may be 4 hours or greater, preferably 6 hours or greater.

In certain embodiments, the time at which oxycodone blood levels reach their maximum concentration ($T_{max}$) is about 2 to about 17 hours, preferably about 6.5 hours to about 17 hours, more preferably about 8 to about 16 hours, and even more preferably about 10 to about 16 or about 12 to about 16 hours after administration at steady state of the dosage form.

In certain embodiments of the present invention, the dosage form provides a $C_{24}/C_{max}$ ratio after administration at steady state of 0.6 to 1.0, a ratio 0.7 to 0.99 or a ratio of 0.8 to 0.95. In other embodiments of the present invention, the dosage form provides a $C_{24}/C_{max}$ ratio after administration at steady state of 0.7 to 1.0, a ratio 0.72 to 0.99 or a ratio of 0.74 to 0.95.

In certain embodiments of the present invention, the dosage form provides a $C_{24}/C_{max}$ ratio after administration at steady state of 0.6 to 1.0, a ratio 0.7 to 0.99 or a ratio of 0.8 to 0.95 and a ($T_{max}$) of about 6.5 hours to about 17 hours, about 8 to about 16 hours, about 10 to about 16 hours or about 12 hours to about 16 hours. In other embodiments of the present invention, the dosage form provides a $C_{24}/C_{max}$ ratio after administration at steady state of 0.7 to 1.0, a ratio 0.72 to 0.99 or a ratio of 0.74 to 0.95 and a ($T_{max}$) in about 2 to about 17 hours.

In certain embodiments of the present invention, the co-administration of food will not significantly increase or decrease the extent of oxycodone absorption.

The sustained release oral dosage form of the present invention includes from about 1 to about 640 mg of oxycodone or a pharmaceutically acceptable salt thereof (e.g., oxycodone hydrochloride). Preferably the sustained release oral dosage form of the present invention includes from about 5 to about 500 mg oxycodone or a pharmaceutically acceptable salt thereof, more preferably from about 10 to about 320 mg oxycodone or a pharmaceutically acceptable salt thereof and even more preferably from about 10 to about 160 mg oxycodone or a pharmaceutically acceptable salt thereof.

In other preferred embodiments, the sustained release dosage form of the present invention comprises from about 10 to about 160 mg oxycodone hydrochloride or an equivalent amount of oxycodone or a pharmaceutically acceptable salt thereof other than the hydrochloride salt.

The present invention includes a method for administering from about 1 to about 640 mg of oxycodone or a pharmaceutically acceptable salt thereof on a once-a-day basis to a patient in need of relief of pain, in accordance with the pharmacokinetic parameters disclosed herein. Preferably, the method includes administering from about 5 to about 500 mg oxycodone or a pharmaceutically acceptable salt thereof.

The method of administration according to the present invention is particularly applicable to the treatment of acute and chronic pain, particularly pain associated with terminal disease such as cancer; chronic backpain; and post-operative pain.

Dosage Forms

In certain embodiments the oral dosage form includes a sustained-release material which is incorporated into a matrix along with the oxycodone or pharmaceutically acceptable salt thereof to provide for the sustained release of the oxycodone. The sustained-release material may be hydrophobic or hydrophilic as desired. The oral dosage form of the present invention may be prepared as granules, spheroids, matrix multiparticulates, etc. which comprise oxycodone or a pharmaceutically acceptable salt thereof in a sustained release matrix, which may be compressed into a tablet or encapsulated. The oral dosage form of the present invention may optionally include other pharmaceutically acceptable ingredients (e.g., diluents, binders, colorants, lubricants, etc.).

In certain embodiments, the oral dosage form of the present invention may be an osmotic dosage form having a push or displacement composition as one of the layers of a bilayer core for pushing oxycodone or a pharmaceutically acceptable salt thereof from the dosage form, and a semipermeable wall composition surrounding the core, wherein the wall has at least one exit means or passageway for delivering the oxycodone from the dosage form. Alternatively, the core of the osmotic dosage form may comprise a single layer core including a controlled release polymer and oxycodone or a pharmaceutically acceptable salt thereof.

Preferably the dosage forms of the present invention provide an analgesic effect for at least about 24 hours after administration.

Sustained-Release Matrix Formulations

In one preferred embodiment of the present invention, the sustained release carrier may be incorporated into a matrix with the oxycodone or pharmaceutically acceptable salt thereof which matrix provides for the sustained release of the oxycodone.

A non-limiting list of suitable sustained-release materials which may be included in a sustained-release matrix according to the invention include hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the oxycodone or pharmaceutically acceptable salt thereof may be used in accordance with the present invention. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly(methacrylic acid), methacrylic acid alkylamine copolymer, poly (methyl methacrylate), poly(methacrylic acid)(anhydride), polymethacrylate, polyacrylamide, poly(methacrylic acid anhydride), and glycidyl methacrylate copolymers. Certain preferred embodiments utilize mixtures of any of the foregoing sustained-release materials in the matrix of the invention.

The matrix also may include a binder. In such embodiments, the binder preferably contributes to the sustained-release of the oxycodone or pharmaceutically acceptable salt thereof from the sustained-release matrix.

If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive. In certain preferred embodiments, a combination of two or more hydrophobic binder materials are included in the matrix formulations.

Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Hydrocarbons having a melting point of between 25° and 90° C. are preferred. Of the long-chain hydrocarbon binder materials, fatty (aliphatic) alcohols are preferred in certain embodiments. The oral dosage form may contain up to 80% (by weight) of at least one digestible, long chain hydrocarbon.

In certain embodiments, the hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C. In certain preferred embodiments, the dosage form comprises a sustained release matrix comprising oxycodone or a pharmaceutically acceptable salt thereof and at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form may be determined, inter alia, by the precise rate of oxycodone or oxycodone salt release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the aliphatic alcohol in the present oral dosage form may be determined, as above, by the precise rate of oxycodone or oxycodone salt release required. It may also depend on whether at least one polyalkylene glycol is present in or absent from the oral dosage form. In the absence of at least one polyalkylene glycol, the oral dosage form preferably contains between about 20% and about 50% (by wt) of the aliphatic alcohol. When a polyalkylene glycol is present in the oral dosage form, then the combined weight of the aliphatic alcohol and the polyalkylene glycol preferably constitutes between about 20% and about 50% (by wt) of the total dosage form.

In one preferred embodiment, the ratio of, e.g., the at least one hydroxyalkyl cellulose or acrylic resin to the at least one aliphatic alcoholpolyalkylene glycol determines, to a considerable extent, the release rate of the oxycodone or oxycodone salt from the formulation. In certain embodiments, a ratio of the hydroxyalkyl cellulose to the aliphatic alcohol/polyalkylene glycol of between 1:1 and 1:4 is preferred, with a ratio of between 1:2 and 1:3 being particularly preferred.

In certain embodiments, the polyalkylene glycol may be, for example, polypropylene glycol, or polyethylene glycol which is preferred. The average molecular weight of the at least one polyalkylene glycol is preferably between 1,000 and 15,000, especially between 1,500 and 12,000.

Another suitable sustained-release matrix comprises an alkylcellulose (especially ethylcellulose), a $C_{12}$ to $C_{36}$ aliphatic alcohol and, optionally, a polyalkylene glycol.

In addition to the above ingredients, a sustained-release matrix may also contain suitable quantities of other materials, e.g., diluents, lubricants, binders, granulating aids, colorants, flavorants and glidants that are conventional in the pharmaceutical art.

In order to facilitate the preparation of a solid, sustained-release oral dosage form according to this invention there is provided, in a further aspect of the present invention, a process for the preparation of a solid, sustained-release oral dosage form according to the present invention comprising incorporating oxycodone or a salt thereof in a sustained-release matrix. Incorporation in the matrix may be effected, for example, by:

(a) forming granules comprising at least one hydrophobic and/or hydrophilic material as set forth above (e.g., a water soluble hydroxyalkyl cellulose) together with the oxycodone or pharmaceutically acceptable salt thereof;

(b) mixing the at least one hydrophobic and/or hydrophilic material-containing granules with at least one $C_{12}$-$C_{36}$ aliphatic alcohol, and (c) optionally, compressing and shaping the granules.

The granules may be formed by any of the procedures well-known to those skilled in the art of pharmaceutical formulation. For example, in one preferred method, the granules may be formed by wet granulating hydroxyalkyl cellulose/oxycodone or oxycodone salt with water. In a particularly preferred embodiment of this process, the amount of water added during the wet granulation step is preferably between 1.5 and 5 times, especially between 1.75 and 3.5 times, the dry weight of the oxycodone or oxycodone salt.

A sustained-release matrix can also be prepared by, e.g., melt-granulation or melt-extrusion techniques. Generally, melt-granulation techniques involve melting a normally solid hydrophobic binder material, e.g., a wax, and incorporating a powdered drug therein. To obtain a sustained release dosage form, it may be necessary to incorporate a hydrophobic sustained-release material, e.g. ethylcellulose or a water-insoluble acrylic polymer, into the molten wax hydrophobic binder material. Examples of sustained-release formulations prepared via melt-granulation techniques are found, e.g., in U.S. Pat. No. 4,861,598.

The additional hydrophobic binder material may comprise one or more water-insoluble wax-like thermoplastic substances possibly mixed with one or more wax-like thermoplastic substances being less hydrophobic than said one or more water-insoluble wax-like substances. In order to achieve sustained release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

The preparation of a suitable melt-extruded matrix according to the present invention may, for example, include the steps of blending the oxycodone or pharmaceutically acceptable salt thereof, together with a sustained release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The matrix multiparticulates are then divided into unit doses. The extrudate preferably has a diameter of from about 0.1 to about 5 mm and provides sustained release of the oxycodone or pharmaceutically acceptable salt thereof for a time period of at least about 24 hours.

An optional process for preparing the melt extruded formulations of the present invention includes directly metering into an extruder a hydrophobic sustained release material, the oxycodone or salt thereof, and an optional binder material; heating the homogenous mixture; extruding the homogenous mixture to thereby form strands; cooling the strands containing the homogeneous mixture; cutting the strands into matrix multiparticulates having a size from about 0.1 mm to about 12 mm; and dividing said particles into unit doses. In this aspect of the invention, a relatively continuous manufacturing procedure is realized.

Plasticizers, such as those described above, may be included in melt-extruded matrices. The plasticizer is preferably included as from about 0.1 to about 30% by weight of the matrix. Other pharmaceutical excipients, e.g., talc, mono or poly saccharides, colorants, flavorants, lubricants and the like may be included in the sustained release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt extruded matrix multiparticulate system can be, for example, in the form of granules, spheroids or pellets depending upon the extruder exit orifice. For purposes of the present invention, the terms "melt-extruded matrix multiparticulate(s)" and "melt-extruded matrix multiparticulate system(s)" and "melt-extruded matrix particles" shall refer to a plurality of units, preferably within a range of similar size and/or shape and containing one or more active agents and one or more excipients, preferably including a hydrophobic sustained release material as described herein. Preferably the melt-extruded matrix multiparticulates will be of a range of from about 0.1 to about 12 mm in length and have a diameter of from about 0.1 to about 5 mm. In addition, it is to be understood that the melt-extruded matrix multiparticulates can be any geometrical shape within this size range. In certain embodiments, the extrudate may simply be cut into desired lengths and divided into unit doses of the therapeutically active agent without the need of a spheronization step.

In one preferred embodiment, oral dosage forms are prepared that include an effective amount of melt-extruded matrix multiparticulates within a capsule. For example, a plurality of the melt-extruded matrix multiparticulates may be placed in a gelatin capsule in an amount sufficient to provide an effective sustained release dose when ingested and contacted by gastrointestinal fluid.

In another embodiment a suitable amount of the multiparticulate extrudate is compressed into an oral tablet using conventional tableting equipment using standard techniques. Techniques and compositions for malting tablets (compressed and molded), capsules (hard and soft gelatin) and pills are also described in *Remington's Pharmaceutical Sciences*, (Arthur Osol, editor), 1553-1593 (1980).

In yet another preferred embodiment, the extrudate can be shaped into tablets as set forth in U.S. Pat. No. 4,957,681 (Klimesch, et. al.).

Optionally, the sustained-release matrix multiparticulate systems, tablets, or capsules can be coated with a sustained release coating such as the sustained release coatings described herein. Such coatings preferably include a sufficient amount of hydrophobic and/or hydrophilic sustained-release material to obtain a weight gain level from about 2 to about 25 percent, although the overcoat may be greater depending upon, e.g., the desired release rate.

The dosage forms of the present invention may further include combinations of melt-extruded matrix multiparticulates containing oxycodone or pharmaceutically acceptable salt thereof. Furthermore, the dosage forms can also include an amount of an immediate release therapeutically active oxycodone or pharmaceutically acceptable salt thereof for prompt therapeutic effect. The immediate release oxycodone or pharmaceutically acceptable salt thereof may be incorporated, e.g., as separate multiparticulates within a gelatin capsule, or may be coated on the surface of, e.g., melt extruded matrix multiparticulates.

The sustained-release profile of the melt-extruded formulations of the invention can be altered, for example, by varying the amount of sustained-release material, by varying the amount of plasticizer relative to other matrix constituents, by varying the amount of hydrophobic material, by the inclusion of additional ingredients or excipients, by altering the method of manufacture, etc.

In other embodiments of the invention, melt-extruded formulations are prepared without the inclusion of the oxycodone or pharmaceutically acceptable salt thereof, which is added thereafter to the extrudate. Such formulations typically will have the oxycodone or pharmaceutically acceptable salt thereof blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and ammeter. In addition, the production system will include a temperature control console which includes temperature sensors, cooling means and temperature indicators throughout the length of the extruder. In addition, the production system will include an extruder such as a twin-screw extruder which consists of two counter-rotating intermeshing screws enclosed within a cylinder or barrel having an aperture or die at the exit thereof. The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the matrix multiparticulate system. The pelletizer can consist of rollers, fixed knife, rotating cutter and the like. Suitable instruments and systems are available from distributors such as C.W. Brabender Instruments, Inc. of South Hackensack, N.J. Other suitable apparatus will be apparent to those of ordinary skill in the art.

A further aspect of the invention is related to the preparation of melt-extruded matrix multiparticulates as set forth above in a manner which controls the amount of air included in the extruded product. By controlling the amount of air included in the extrudate, the release rate of the oxycodone or therapeutically acceptable salt thereof may be altered.

Thus, in a further aspect of the invention, the melt-extruded product is prepared in a manner which substantially excludes air during the extrusion phase of the process. This may be accomplished, for example, by using a Leistritz extruder having a vacuum attachment. The extruded matrix multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Such substantially non-porous formulations may provide a faster release of the therapeutically active agent, relative to the same formulation prepared without vacuum. SEMs of the matrix multiparticulates prepared using an extruder under vacuum appear very smooth, and the multiparticulates tend to be more robust than those multiparticulates prepared without vacuum. It has been observed that in at least certain formulations, the use of extrusion under vacuum provides an extruded matrix multiparticulate product which is more pH-dependent than its counterpart formulation prepared without vacuum.

Alternatively, the melt-extruded product is prepared using a Werner-Pfleiderer twin screw extruder.

In certain embodiments, a spheronizing agent is added to a granulate or matrix multiparticulate and then spheronized to produce sustained release spheroids. The spheroids are then optionally overcoated with a sustained release coating by methods such as those described above.

Spheronizing agents which may be used to prepare the matrix multiparticulate formulations of the present invention include any art-known spheronizing agent. Cellulose derivatives are preferred, and microcrystalline cellulose is especially preferred. A suitable microcrystalline cellulose is, for example, the material sold as Avicel PH 101 (TradeMark, FMC Corporation). The spheronizing agent is preferably included as about 1 to about 99% of the matrix multiparticulate by weight.

In certain embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

In certain embodiments, a sustained release coating is applied to the sustained release spheroids, granules, or matrix multiparticulates. In such embodiments, the sustained-release coating may include a water insoluble material such as (a) a wax, either alone or in admixture with a fatty alcohol; or (b) shellac or zein. The coating is preferably derived from an aqueous dispersion of the hydrophobic sustained release material.

In certain embodiments, it is necessary to overcoat the sustained release spheroids, granules, or matrix multiparticulates comprising the oxycodone or pharmaceutically acceptable salt thereof and sustained release carrier with a sufficient amount of the aqueous dispersion of, e.g., alkylcellulose or acrylic polymer, to obtain a weight gain level from about 2 to about 50%, e.g., about 2 to about 25%, in order to obtain a sustained-release formulation. The overcoat may be lesser or greater depending upon, e.g., the desired release rate, the inclusion of plasticizer in the aqueous dispersion and the manner of incorporation of the same. Cellulosic materials and polymers, including alkylcelluloses, are sustained release materials well suited for coating the sustained release spheroids, granules, or matrix multiparticulates according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly to the sustained release spheroids, granules, or matrix multiparticulates.

In other preferred embodiments of the present invention, the sustained release material comprising the sustained-release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in the National Formulary (NF) XVII as fully polymerized copolymers of acrylic and methacrylic acid esters with a low content of quaternary ammonium groups. In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm GMBH and Co. Kg Darmstadt, Germany. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent; however, dosage forms coated with Eudragit RL and RS are pH-independent.

In certain preferred embodiments, the acrylic coating comprises a mixture of two acrylic resin lacquers commercially available from Rohm under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dissolution profile. Desirable sustained-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L. In embodiments of the present invention where the coating comprises an aqueous dispersion of a hydrophobic sustained release material, the inclusion of an effective amount of a plasticizer in the aqueous dispersion of hydrophobic material will further improve the physical properties of the sustained-release coating. For example, because ethylcellulose has a relatively high glass transition temperature and does not form flexible films under normal coating conditions, it is preferable to incorporate a plasticizer into an ethylcellulose coating containing sustained-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

In certain embodiments, the uncoated/coated sustained release spheroids, granules, or matrix multiparticulates containing the oxycodone or oxycodone salt are cured until an endpoint is reached at which the sustained release spheroids, granules, or matrix multiparticulates provide a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. Cured formulations are described in detail in U.S. Pat. Nos. 5,273,760; 5,286,493; 5,500,227; 5,580,578; 5,639,476; 5,681,585; and 6,024,982. Other examples of sustained-release formulations and coatings which may be used in accordance with the present invention include U.S. Pat. Nos. 5,324,351; 5,356,467; and 5,472,712.

In addition to the above ingredients, the spheroids, granules, or matrix multiparticulates may also contain suitable quantities of other materials, e.g., diluents, lubricants, binders, granulating aids, colorants, flavorants and glidants that are conventional in the pharmaceutical art in amounts up to about 50% by weight of the formulation if desired. The quantities of these additional materials will be sufficient to provide the desired effect to the desired formulation.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

It has further been found that the addition of a small amount of talc to the sustained release coating reduces the tendency of the aqueous dispersion to stick during processing, and acts as a polishing agent.

Sustained Release Osmotic Dosage

Sustained release dosage forms according to the present invention may also be prepared as osmotic dosage formulations. The osmotic dosage forms preferably include a bilayer core comprising a drug layer and a delivery or push layer, wherein the bilayer core is surrounded by a semipermeable wall and optionally having at least one passageway disposed therein.

The expression "passageway" as used for the purpose of this invention, includes aperture, orifice, bore, pore, porous element through which oxycodone or oxycodone salt can be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The passageway can have any shape, such as round, triangular, square and elliptical, for assisting in the sustained metered release of oxycodone or oxycodone salt from the dosage form. The dosage form can be manufactured with one or more passageways in spaced-apart relation on one or more surfaces of the dosage form. A passageway and equipment for forming a passageway are disclosed in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are disclosed in U.S. Pat. Nos. 4,200,098 and 4,285,987.

In certain embodiments, the bilayer core comprises a drug layer with oxycodone or a salt thereof and a displacement or push layer. In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the oxycodone or pharmaceutically acceptable salt thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropylisopropylcellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a homogenous core comprising oxycodone or a pharmaceutically acceptable salt thereof, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the oxycodone or pharmaceutically acceptable salt thereof.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable crosslinked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm$^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

In certain preferred embodiments, the present invention includes a therapeutic composition comprising 1 to 640 mg of the oxycodone or pharmaceutically acceptable salt thereof, 25 to 500 mg of poly(alkylene oxide) having a 150,000 to 500,000 average molecular weight, 1 to 50 mg of poly(vinylpyrrolidone) having a 40,000 average molecular weight, and 0 to about 7.5 mg of a lubricant.

In certain embodiments, the invention also provides a method for administering 1 to 640 mg of oxycodone or a pharmaceutically acceptable salt thereof by admitting orally 1 to 640 mg of oxycodone or pharmaceutically acceptable salt thereof to a patient administered from a dosage form comprising a semipermeable wall permeable to aqueous-biological fluid and impervious to the passageway of oxycodone or pharmaceutically acceptable salt thereof, which semipermeable wall surrounds an internal space comprising an oxycodone drug composition and a push composition, said oxycodone drug composition comprising 1 to 640 mg of oxycodone or pharmaceutically acceptable salt thereof, 25 to 500 mg of a poly(alkylene oxide) having a 150,000 to 500,000 average molecular weight, 1 to 50 mg of a poly(vinylpyrrolidone) having a 40,000 average molecular weight, and 0 to 7.5 mg of a lubricant, said push composition comprising 15 to 250 mg of a poly(alkylene oxide) of 3,000,000 to 7,500,000 average molecular weight, 0 to 75 mg of an osmagent, 1 to 50 mg of a hydroxyalkylcellulose, 0 to 10 mg of ferric oxide, 0 to 10 mg of a lubricant, and 0 to 10 mg of antioxidant; and a passageway in the semipermeable wall for delivering the oxycodone or pharmaceutically acceptable salt thereof from the dosage form, by imbibing fluid through the semipermeable wall into the dosage form causing the oxycodone or oxycodone salt composition to become dispensable and the push composition to expand and push the oxycodone or oxycodone salt composition through the passageway, whereby through the combined operations of the dosage form, the oxycodone or oxycodone salt is delivered at a therapeutically effective dose at a rate controlled over a sustained period of time.

The dosage forms of the present invention may optionally be coated with one or more coatings suitable for the regulation of release or for the protection of the formulation. In one embodiment, coatings are provided to permit either pH-dependent or pH-independent release, e.g., when exposed to gastrointestinal (GI) fluid. When a pH-independent coating is desired, the coating is designed to achieve optimal release regardless of pH-changes in the environmental fluid, e.g., the GI tract. Other preferred embodiments include a pH-dependent coating that releases the oxycodone or pharmaceutically acceptable salt thereof in desired areas of the GI tract, e.g., the stomach or small intestine, such that an absorption profile is provided which is capable of providing at least about twelve hours and preferably about twenty-four hours or more of analgesia to a patient. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings may also impart a repeat-action effect whereby unprotected drug is coated over an enteric coat and is released in the stomach, while the remainder, being protected by the enteric coating, is released further down the gastrointestinal tract. Coatings which are pH-dependent and may be used in accordance with the present invention include a sustained release material such as, e.g., shellac, cellulose acetate phthalate (CAP), polyvinyl acetate phthalate (PVAP), hydroxypropyl methylcellulose phthalate, and methacrylic acid ester copolymers, zein, and the like.

In certain embodiments of the present invention, an effective amount of oxycodone or pharmaceutically acceptable salt thereof in immediate release form is included in the formulation. The immediate release form of the oxycodone or oxycodone salt is included in an amount which is effective to reduce the time to maximum concentration of the oxycodone in the blood (e.g., plasma), such that the $T_{max}$ is reduced. By including such an effective amount of immediate release oxycodone or oxycodone salt in the unit dose, the experience of relatively higher levels of pain in patients may be reduced. In such embodiments, an effective amount of the oxycodone or oxycodone salt in immediate release form may be coated onto the tablet of the present invention. For example, where the extended release oxycodone or oxycodone salt from the formulation is due to a sustained release coating, the immediate release layer would be overcoated on top of the sustained release coating. On the other hand, the immediate release layer may be coated onto the surface of tablets wherein the oxycodone or oxycodone salt is incorporated in a sustained release matrix. One skilled in the art would recognize still other alternative manners of incorporating the immediate release oxycodone or oxycodone salt portion into the formulation. Such alternatives are deemed to be encompassed by the appended claims.

In yet further embodiments, the sustained release dosage forms of the present invention in addition to oxycodone or oxycodone salt may further include a non-opioid drug which may or may not act synergistically with the oxycodone or oxycodone salt. Such non-opioid drugs would preferably provide additional analgesia, and include, for example, aspirin; acetaminophen; non-steroidal anti-inflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cyclooxygenase-II inhibitors ("COX-II inhibitors"); and/or glycine receptor antagonists.

In certain embodiments of the present invention, the invention allows for the use of lower doses of oxycodone or oxycodone salt by virtue of the inclusion of an additional non-opioid analgesic, such as an NSAID or a COX-2 inhibitor. By using lower amounts of either or both drugs, the side effects associated with effective pain management in humans may be reduced.

Suitable non-steroidal anti-inflammatory agents, include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof, mixtures thereof, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, or pharmaceutically acceptable salts thereof. For purposes of the present invention, the term "NMDA antagonist" is also deemed to encompass drugs that at least partially inhibit a major intracellular consequence of NMDA-receptor activation, e.g. a ganglioside such as $GM_1$ or $GT_{1b}$, a phenothiazine such as trifluoperazine or a naphthalenesulfonamide such as N-(6-aminothexyl)-5-chloro-1-naphthalenesulfonamide.

These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al.). The NMDA antagonist may be included alone, or in combination with a local anesthetic such as lidocaine, as described in these Mayer, et al. patents.

The treatment of chronic pain via the use of glycine receptor antagonists and the identification of such drugs is described in U.S. Pat. No. 5,514,680 (Weber, et al.).

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311. Certain preferred COX-2 inhibitors include celecoxib (SC-58635), DUP-697, flosulide (CGP-28238), meloxicam, 6-methoxy-2 naphthylacetic acid (6-MNA), MK-966 (also known as Vioxx), nabumetone (prodrug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per day are therapeutically effective in combination with oxycodone or oxycodone salt. Alternatively, about 0.25 mg to about 7 g per patient per day of a COX-2 inhibitor is administered in combination with oxycodone or oxycodone salt.

In yet further embodiments, a non-opioid drug can be included which provides a desired effect other than analgesia, e.g., antitussive, expectorant, decongestant, antihistamine drugs, local anesthetics, and the like.

The additional (non-opioid) therapeutically active agent may be included in sustained release form or in immediate release form. The additional drug may be incorporated into the sustained release matrix along with the oxycodone or oxycodone salt, may be incorporated as a powder, granulation, etc. into the dosage form, or may be incorporated as a separated sustained release layer or immediate release layer.

The sustained-release oral solid dosage forms of the present invention may be opioid-sparing. It is possible that the sustained-release oral solid dosage forms of the present invention may be dosed at a substantially lower daily dosage in comparison to conventional immediate-release products, with no significant difference in analgesic efficacy. At comparable daily dosages, greater efficacy may result with the use of sustained-release oral solid dosage forms of the present invention in comparison to conventional immediate-release products.

The present invention will now be more fully described with reference to the accompanying examples. It should be understood, however, that the following description is illustrative only and should not be taken in any way as a restriction on the generality of the invention specified above.

EXAMPLE 1

Oxycodone sustained release matrix tablets are produced with the formula set forth in Table 1 below:

TABLE 1

| Ingredient | Amt/unit (mg) | Amt/batch (gram) |
|---|---|---|
| Oxycodone HCl | 30.0 | 150.0 |
| Spray Dried Lactose | 50.0 | 250.0 |
| Povidone | 8.0 | 40.0 |
| Eudragit RS30D (Solids) | 50.0 | 250.0 |
| Triacetin | 6.0 | 30.0 |
| Stearyl Alcohol | 70.0 | 350.0 |
| Talc | 4.0 | 20.0 |
| Magnesium Stearate | 2.0 | 10.0 |
| Opadry Red YS1-15597-A | 10.0 | 50.0 |
| Purified Water | * | * |
| Total | 230.0 | 1150.0 |

* Used for processing and remains in product as residual moisture only.

According to the following procedure:
1. Granulation: Spray the Eudragit/Triacetin dispersion onto the Oxycodone HCl, Spray Dried Lactose and Povidone using a fluid bed granulator.
2. Milling: Discharge the granulation and pass through a mill with approximately 1 mm openings (18 mesh screen).
3. Waxing: Melt the stearyl alcohol at about 50 degrees C. and add to the milled granulation using a high shear mixer. Allow to cool to room temperature on trays or a fluid bed.
4. Milling: Pass the cooled granulation through a mill with an approximately 18 mesh screen.
5. Lubrication: Lubricate the granulation with talc and magnesium stearate using a mixer.
6. Compression: Compress the granulation into tablets using a Kilian® Tablet press.
7. Film Coating: Apply an aqueous film coat to the tablets using a rotary pan.

EXAMPLE 2

Oxycodone sustained release osmotic tablets are produced with the formula set forth in Table 2 below:

TABLE 2

| Ingredient | Amt/unit (mg) |
|---|---|
| Drug Layer: | |
| Oxycodone HCl | 35.20 |
| Polyethylene oxide | 130.24 |
| Povidone | 8.8 |
| Magnesium Stearate | 1.76 |
| Displacement Layer: | |
| Polyethylene oxide | 85.96 |
| Sodium chloride | 40.50 |
| Hydroxypropylmethylcellulose | 6.75 |
| Ferric Oxide | 1.35 |
| Magnesium Stearate | 0.34 |
| BHT | 0.10 |
| Semipermeable Wall: | |
| Cellulose acetate | 38.6 |

The dosage form having the above formulation is prepared according to the following procedure:

First, 175 g of oxycodone hydrochloride, 647.5 g of poly (ethylene oxide) possessing a 200,000 average molecular weight, and 43.75 g of poly(vinylpyrrolidone) having a 40,000 average molecular weight is added to a mixer and mixed for 10 minutes. Then, 331 g of denatured anhydrous alcohol is added to the blended materials with continuous mixing for 10 minutes. Then, the wet granulation is passed through a 20 mesh screen, allowed to dry at room temperature for 20 hours, and then passed through a 16 mesh screen. Next, the granulation is transferred to the mixer, mixed and lubricated with 8.75 g of magnesium stearate.

Then, the displacement or push composition for pushing the oxycodone HCl composition from the dosage form is prepared as follows: first 3910 g of hydroxypropylmethylcellulose possessing an 11,200 average molecular weight is dissolved in 45,339 g of water. Then, 101 g of butylated hydroxytoluene is dissolved in 650 g of denatured anhydrous alcohol. Next, 2.5 kg of the hydroxypropylmethylcellulose aqueous solution is added with continuous mixing to the butylated hydroxytoluene alcohol solution. Then, binder solution preparation is completed by adding with continuous mixing the remaining hydroxypropylmethylcellulose aqueous solution to the butylated hydroxytoluene alcohol solution.

Next, 36,000 g of sodium chloride is sized using a Quadro Comil® mill equipped with a 21 mesh screen. Then, 1200 g of ferric oxide is passed through a 40 mesh screen. Then, the screened materials, 76,400 g of pharmaceutically acceptable poly(ethylene oxide) possessing a 7,500,000 average molecular weight, 2500 g of hydroxypropylmethylcellulose having a 11,200 average molecular weight are added to a Glatt® Fluid Bed Granulation's bowl. The bowl is attached to the granulator and the granulation process is initiated for effecting granulation. Next, the dry powders are air suspended and mixed for 10 minutes. Then, the binder solution is sprayed from 3 nozzles onto the powder. The granulating is monitored during the process as follows: total solution spray rate of 800 g/min; inlet temperature 43° C. and air flow 4300 $m^3$/hr. At the end of solution spraying, 45,033 g, the resultant coated granulated particles are subjected to a drying process for 35 minutes.

The coated granules are sized using a Quadro Comil® mill with an 8 mesh screen. The granulation is transferred to a Tote® Tumbler, mixed and lubricated with 281.7 g of magnesium stearate.

Next, the drug composition comprising the oxycodone hydrochloride and the push composition are compressed into bilayer tablets on a Kilian® Tablet press. First, 176 mg of the oxycodone hydrochloride composition is added to the die cavity and precompressed, then, 135 mg of the push composition is added and the layers are pressed under a pressure head of 3 metric tons into an 11/32 inch (0.873 cm) diameter contacting layer arrangement.

The bilayered arrangements are coated with a semipermeable wall. The wall forming composition comprises 100% cellulose acetate having a 39.8% acetyl content. The wall-forming composition is dissolved in acetone:water (95:5 wt:wt) cosolvent to make a 4% solid solution. The wall-forming composition is sprayed onto and around the bilayers in a 24 inch (60 cm) Vector® Hi-Coater. Next, one 20 mil (0.508 mm) exit passageway is drilled through the semipermeable wall to connect the drug oxycodone layer with the exterior of the dosage form. The residual solvent is removed by drying for 72 hours at 45° C. and 45% humidity. Next, the osmotic dosage systems are dried for 4 hours at 45° C. to remove excess moisture. The dosage forms produced by this manufacture comprises 35.20 mg of oxycodone HCl, 130.24 mg of poly(ethylene oxide) of 200,000 average molecular weight, 8.80 mg of poly(vinylpyrrolidone) of 40,000 average molecular weight, and 1.76 mg of magnesium stearate. The push composition comprises 85.96 mg of poly(ethylene oxide) of 7,500,000 average molecular weight, 40.50 mg of sodium chloride, 6.75 mg of hydroxypropylmethylcellulose, 1.35 mg of red ferric oxide, 0.34 mg of magnesium stearate, and 0.10 mg of butylated hydroxytoluene. The semipermeable wall comprises 38.6 mg of cellulose acetate comprising a 39.8% acetyl content. The dosage form comprises one passageway, 20 mil (0.508 mm).

EXAMPLE 3

Oxycodone sustained release osmotic tablets are produced with the formula set forth in Table 3 below:

TABLE 3

| Ingredient<br>Drug Layer: | Percentage<br>Percentage of Drug Layer |
|---|---|
| Oxycodone HCL | 28.8 |
| Polyethylene oxide | 64.2 |
| Povidone | 6 |
| Magnesium Stearate | 1 |

| Displacement Layer: | Percentage of Displacement Layer |
|---|---|
| Polyethylene oxide | 63.675 |
| Sodium chloride | 30 |
| Hydroxypropylmethylcellulose | 5 |
| Ferric Oxide | 1 |
| Magnesium Stearate | 0.25 |
| BHT | 0.075 |

| Semipermeable Wall: | Percentage of Semipermeable Wall |
|---|---|
| Cellulose acetate | 95 |
| Polyethylene glycol | 5 |

The dosage form having the above formulation is prepared according to the following procedure:

First, 1728 g of oxycodone HCl, 3852 g of poly(ethylene oxide) possessing a 200,000 average molecular weight, and 360 g of poly(vinyl pyrrolidone) having an average molecular weight of 40,000 are added to a planetary mixing bowl. Next, the dry materials are mixed for ten minutes. Then, 1616 g of denatured anhydrous ethyl alcohol is slowly added to the blended materials with continuous mixing for 15 minutes. Next, the freshly prepared wet granulation is passed through a 20 mesh screen, allowed to dry at room temperature for 20.5 hours, and passed through a 16 mesh screen. Next, the granulation is transferred to a planetary mixer, mixed and lubricated with 59.8 g of magnesium stearate.

Next, a push composition is prepared as follows: first, a binder solution is prepared by dissolving 3910 g of hydroxypropylmethylcellulose possessing an average molecular weight of 11,200 in 45,339 g of water. Next, 101 g of butylated hydroxytoluene is dissolved in 650 g of denatured anhydrous alcohol. Approximately 2.5 kg of the hydroxypropylmethylcellulose/water solution is added to the butylated hydroxytoluene/alcohol solution with continuous mixing. Next, the binder solution preparation is completed by adding the remaining hydroxypropyl-methylcellulose/water solution to the butylated hydroxyl-toluene/alcohol solution, again with continuous mixing.

Next, 36,000 g of sodium chloride is sized using a Quadro Comil® mill, used to reduce the particle size of the sodium chloride. A fluid air mill is another mill used to size materials with a 21 mesh screen. Next, 1200 g of ferric oxide is passed through a 40 mesh screen. Then, all the screened materials, 76,400 g of pharmaceutically acceptable poly(ethylene oxide) comprising a 7,000,000 average molecular weight, 2520 g of hydroxypropylmethylcellulose comprising an average molecular weight of 11,200 is added to a Glatt Fluid Bed Granulator bowl. The bowl is attached to the granulator and the granulation process is initiated for effecting granulation. Next, the dry powders are air suspended and mixed for 10 minutes. Then, the binder solution is sprayed from 3 nozzles onto the powder.

While spraying the binder solution, the filter bags are shaken for 10 seconds every 1.5 minutes to unglue any possible powder deposits. At the end of the solution spraying, 45,033 g of the resultant coated granulated particles are subjected to a drying process for 35 minutes. The machine is turned off, and the coated granules are removed from the granulator. The coated granules are sized using a Quadro Comil with an 8 mesh screen. The granulation is transferred to Tote Tumbler, mixed and lubricated with 281.7 g of magnesium stearate. Please review second sentence and clarify.

Next, the oxycodone HCl drug composition and the push composition are compressed into bilayer tablets on the Kilian® Tablet Press. First, 434 mg of the oxycodone HCl composition is added to the die cavity and pre-compressed, then, 260 mg of the push composition is added and the layers are pressed under a pressure head of approximately 3 metric tons into a 0.700" (1.78 cm)×0.375" (0.95 cm) oval contacting layered arrangement.

The bilayered arrangement is coated with a semi-permeable wall. The wall forming composition comprises 95% cellulose acetate having a 39.8% acetyl content, and 5% polyethylene glycol having a molecular weight of 3350. The wall-forming composition is dissolved in an acetone:water (95:5 wt:wt) cosolvent to make a 4% solids solution. The wall-forming composition is sprayed onto and around the bilayers in a 24" Vector Hi® Coater.

Next, two 30 mil (0.762 mm) exit passageways are drilled through the semipermeable wall to connect the drug layer with the exterior of the dosage system. The residual solvent is removed by drying for 48 hours at 50° C. and 50% humidity. Next, the osmotic dosage forms are dried for 4 hours at 50° C. to remove excess moisture. The dosage form produced by this manufacture provides 28.8% oxycodone HCl, 64.2% poly (ethylene oxide) possessing a 200,000 average molecular weight, 6% poly(vinyl pyrrolidone) possessing a 40,000 average molecular weight, and 1% magnesium stearate. The push composition comprises 63.675% poly(ethylene oxide) comprising a 7,000,000 average molecular weight, 30% sodium chloride, 5% hydroxypropylmethylcellulose comprising a 11,200 average molecular weight, 1% ferric oxide, 0.075% butylated hydroxytoluene, and 0.25% magnesium stearate. The semipermeable wall comprises 95 wt % cellulose acetate comprising a 39.8% acetyl content, and 5.0 wt % polyethylene glycol comprising a 3350 average molecular weight. The dosage form comprises two passageways, 30 mils (0.762 mm), and has an oxycodone hydrochloride mean release rate of about 5 mg/hr.

The dosage form in further embodiments can comprise 65 wt % to 100 wt % of a cellulose polymer which polymer comprises a member selected from the group consisting of a cellulose ester, cellulose diester, cellulose triester, cellulose ether, cellulose ester-ether, cellulose acylate, cellulose diacylate, cellulose triacetate, cellulose acetate butyrate, and the like. The wall can also comprise from 0 wt % to 40 wt % of a cellulose ether member selected from the group consisting of hydroxypropylcellulose and hydroxypropylmethylcellulose and from 0 wt % to 20 wt % of polyethylene glycol. The total amount of all components comprising the wall is equal to 100 wt %. Semipermeable polymers useful for manufacturing wall of the dosage form are disclosed in U.S. Pat. Nos. 3,845,770; 3,916,899; 4,008,719; 4,036,228; and 4,111,201.

The wall in other preferred processes comprises the selectively permeable cellulose ether, ethyl cellulose. The ethyl cellulose comprises an ethoxy group with a degree of substitution, of about 1.4 to 3, equivalent to 40% to 50% ethoxy content, and a viscosity range of 7 to 100 centipoise, or higher. More specifically, the wall comprises 45 wt % to 80 wt % ethyl cellulose, from 5 wt % to 30 wt % hydroxypropylcellulose, and from 5 wt % to 30 wt % polyethylene glycol, with the total weight percent of all components comprising the wall equal to 100 wt %. In another embodiment the wall comprises 45 wt % to 80 wt % of ethylcellulose, from 5 wt % to 30 wt % hydroxypropylcellulose, from 2 wt % to 20 wt % of polyvinyl pyrrolidone, with the total amount of all components comprising the wall equal to 100 wt %.

EXAMPLE 4

Oxycodone 10 mg sustained release capsules were prepared with the formula set forth in Table 4 below:

TABLE 4

| Ingredient | Amt/unit (mg) |
| --- | --- |
| Oxycodone HCl | 10.0 |
| Stearic Acid | 8.25 |
| Stearic Alcohol | 24.75 |
| Eudragit RSPO | 77 |
| Total | 120 |

The formulation above was prepared according to the following procedure:

1. Pass the stearyl alcohol flakes through an impact mill.
2. Blend the Oxycodone HCl, stearic acid, stearyl alcohol and the Eudragit RSPO in a suitable blender/mixer.
3. Continuously feed the blended material into a twin screw extruder at elevated temperatures, and collect the resultant strands on a conveyor.
4. Allow the strands to cool on the conveyor.
5. Cut the strands into 1 mm pellets using a pelletizer.
6. Screen the pellets for fines and oversized pellets to an acceptable range of about 0.8-1.4 mm in size.
7. Fill into capsules with a fill weight of 120 mg/capsule (fill into size 2 capsules).

The pellets were then tested for dissolution using the following procedure: Fiber optic UV dissolution using USP apparatus 1 (basket) at 100 rpm in 900 ml simulated gastric fluid (SGF) and in 900 ml simulated intestinal fluid (SIF) monitoring at 282 nm.

The dissolution parameters are set forth in Table 4A below:

TABLE 4A

| Time (hour) | % Dissolved in SGF | % Dissolved in SIF |
| --- | --- | --- |
| 1 | 15 | 10 |
| 2 | 22 | 15 |
| 4 | 32 | 22 |
| 8 | 44 | 29 |
| 12 | 53 | 34 |
| 18 | 62 | 40 |
| 24 | 66 | 44 |

EXAMPLE 5

Oxycodone 160 mg sustained release capsules were prepared with the formula set forth in Table 5 below:

TABLE 5

| Ingredient | Amt/unit (mg) |
| --- | --- |
| Oxycodone HCL | 160 |
| Stearic Acid | 80 |
| Stearyl Alcohol | 20 |
| Eudragit RSPO | 140 |
| Total | 400 |

The formulation above was prepared according to the following procedure:

1. Pass the stearyl alcohol flakes through an impact mill.
2. Blend the Oxycodone HCl, stearic acid, stearyl alcohol and the Eudragit RSPO in a suitable lender/mixer.
3. Continuously feed the blended material into a twin screw extruder at elevated temperatures and collect the resultant strands on a conveyor.
4. Allow the strands to cool on the conveyor.
5. Cut the strands into 1 mm pellets using a pelletizer.
6. Screen the pellets for fines and oversized pellets to an acceptable range of about 0.8-1.4 mm in size.
7. Fill into capsules with a fill weight of 400 mg/capsule (Fill into size 00 capsules).

Dissolution Method:

The pellets were then tested for dissolution using the following procedure:

Fiber optic UV dissolution using USP apparatus 1 (basket) at 100 rpm in 900 ml simulated gastric fluid (SGF) and in 900 ml simulated intestinal fluid (SIF) monitoring at 282 nm.

The dissolution parameters for the above formulation are set forth in Table 5A below: Please ensure Table 5A does not have error message.

TABLE 5A

| Time (hour) | % Dissolved in SGF | % Dissolved in SIF |
|---|---|---|
| 1 | 32 | 20 |
| 2 | 47 | 28 |
| 4 | 66 | 42 |
| 8 | 86 | 60 |
| 12 | 93 | 70 |
| 18 | 95 | 77 |
| 24 | 95 | 80 |

Many other variations of the present invention will be apparent to those skilled in the art and are meant to be within the scope of the claims appended hereto.

What is claimed is:

1. A sustained-release oral dosage form for once-a-day administration comprising:
    a pharmaceutically acceptable matrix comprising an analgesically effective amount of oxycodone or a pharmaceutically acceptable salt thereof and a sustained release material, said dosage form providing an analgesic effect for at least about 24 hours after oral administration at steady state to human patients; and
    said dosage form providing a mean $C_{24}/C_{max}$ oxycodone ratio of 0.7 to 1.0 and a mean $T_{max}$ of about 6.5 to about 17 hours after steady state oral administration to said patients.

2. The dosage form of claim 1, wherein the matrix is substantially homogeneous.

3. The dosage form of claim 1, wherein said matrix is contained within a gelatin capsule.

4. The dosage form of claim 1, wherein said matrix is formulated into a tablet.

5. The dosage form of claim 1, wherein said amount is from about 5 to about 640 mg.

6. The dosage form of claim 1, wherein said pharmaceutically acceptable salt of oxycodone is oxycodone hydrochloride.

7. The dosage form of claim 1, which provides a mean $C_{24}/C_{max}$ ratio of 0.7 to 0.99 after administration at steady state to said patients.

8. The dosage form of claim 1, which provides a mean $C_{24}/C_{max}$ ratio of 0.8 to 0.95 after administration at steady state to said patients.

9. The dosage form of claim 1, which provides an in-vitro release rate, of oxycodone or a pharmaceutically acceptable salt thereof, when measured by the USP Basket Method at 100 rpm in 900 ml aqueous buffer at a pH of between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hrs, and greater than about 50% at 24 hours.

10. A sustained-release oral dosage form for once-a-day administration comprising:
    a pharmaceutically acceptable matrix comprising an analgesically effective amount of oxycodone or a pharmaceutically acceptable salt thereof and a sustained release material, said dosage form providing an analgesic effect for at least about 24 hours after oral administration at steady state to human patients; and
    said dosage form providing a mean $C_{24}/C_{max}$ oxycodone ratio of 0.74 to 0.95 and a mean $T_{max}$ at about 6.5 to about 17 hours after oral administration at steady state to said patients.

11. A sustained-release oral dosage form for once-a-day administration comprising:
    a pharmaceutically acceptable matrix comprising an analgesically effective amount of oxycodone or a pharmaceutically acceptable salt thereof and a sustained release material, said dosage form providing an analgesic effect for at least about 24 hours after oral administration at steady state to human patients; and
    said dosage form providing a mean $C_{24}/C_{max}$ oxycodone ratio of 0.72 to 0.99 and a mean $T_{max}$ at about 6.5 to about 17 hours after oral administration at steady state to said patients.

12. A method of preparing a sustained release dosage form comprising incorporating oxycodone or a pharmaceutically acceptable salt thereof and a sustained release material into a pharmaceutically acceptable matrix, and preparing the dosage form comprising the matrix, such that the dosage form provides an analgesic effect for at least about 24 hours, a mean $C_{24}/C_{max}$ oxycodone ratio of 0.7 to 1.0 and a mean $T_{max}$ at about 6.5 to about 17 hours after administration at steady state to human patients.

13. The dosage form of any one of claims 1, 2, 3, 4, 5, 6, 7, 8, 9, 10, or 11 which provides a mean $T_{max}$ of oxycodone at about 10 to about 16 hours after administration at steady state to said patients.

14. The dosage form of any one of claims 1, 2, 3, 4, 5, 6, 7, 8, 9, 10, or 11 which provides a mean $T_{max}$ of oxycodone at about 12 to about 16 hours after administration at steady state to said patients.

15. The dosage form of claim 1, wherein said oxycodone is the only active agent in the dosage form.

16. The dosage form of claim 10, wherein said oxycodone is the only active agent in the dosage form.

17. The dosage form of claim 11, wherein said oxycodone is the only active agent in the dosage form.

* * * * *